(12) United States Patent
Goldberg et al.

(10) Patent No.: US 12,274,569 B2
(45) Date of Patent: Apr. 15, 2025

(54) SYSTEM AND METHOD FOR PERFORMING SPIRAL-TRAJECTORY TOMOSYNTHESIS

(71) Applicant: Orimtech Ltd., Buffalo Grove, IL (US)

(72) Inventors: Boris S. Goldberg, Buffalo Grove, IL (US); Serguei Gouzeev, Discovery Bay, CA (US)

(73) Assignee: Orimtech, Ltd., Buffalo Grove, IL (US)

( * ) Notice: Subject to any disclaimer, the term of this patent is extended or adjusted under 35 U.S.C. 154(b) by 0 days.

(21) Appl. No.: 17/344,404

(22) Filed: Jun. 10, 2021

(65) Prior Publication Data

US 2021/0393217 A1 Dec. 23, 2021

Related U.S. Application Data

(60) Provisional application No. 63/037,681, filed on Jun. 11, 2020.

(51) Int. Cl.
*A61B 6/02* (2006.01)
*A61B 6/00* (2024.01)
*A61B 6/50* (2024.01)

(52) U.S. Cl.
CPC .............. *A61B 6/027* (2013.01); *A61B 6/025* (2013.01); *A61B 6/4458* (2013.01); *A61B 6/508* (2013.01)

(58) Field of Classification Search
CPC ....... A61B 6/025; A61B 6/027; A61B 6/4458; A61B 6/508
See application file for complete search history.

(56) References Cited

U.S. PATENT DOCUMENTS

| | | | | |
|---|---|---|---|---|
| 8,483,351 | B2 * | 7/2013 | Wang | A61B 6/027 378/4 |
| 2003/0091151 | A1 * | 5/2003 | Horbaschek | A61B 6/4464 378/196 |

(Continued)

OTHER PUBLICATIONS

Miroshnychenko, S & Gouzeev, S & Goldberg, B & Miroshnychenko, Oleksandra & Nevgasymyl, Andrii. (2020). The Concept of the X-Ray Apparatus With Tomosynthesis for Thorax Screening. DOI: 10.13140/RG.2.2.22882.06082. [retrieved Sep. 9, 2021] Retrieved from the Internet. <URL: https://www.researchgate.net/publication/342079056_THE_CONCEPT_OF_THE_X-RAY_APPARATUS_WITH_TOMOSYNTHESIS_FOR_THORAX_SCREENING>.

(Continued)

*Primary Examiner* — Dani Fox
*Assistant Examiner* — Soorena Kefayati
(74) *Attorney, Agent, or Firm* — Bishop & Diehl, Ltd.

(57) ABSTRACT

A tomosynthesis scanning system includes an X-ray emitter connected to a first robotic device, and an X-ray detector connected to a second robotic device. The first robotic device moves the emitter along a first spiral trajectory path and, optionally, the second robotic device moves the detector along a second spiral trajectory path during the scanning process. Where both the emitter and detector move, the movement is synchronized. A computer is used to control the first and second robotic devices. In operation, an object to be scanned is positioned between the X-ray emitter and the X-ray detector, then the X-ray emitter is moved along a first spiral path while emitting a photon beam at the X-ray detector and allowing the photon beam to pass through the object before reaching the X-ray detector. Attenuation of the photon beam reaching the X-ray detector is measured and an image is produced based on the measured attenuation of the photon beam.

12 Claims, 21 Drawing Sheets

(56) References Cited

U.S. PATENT DOCUMENTS

| | | | |
|---|---|---|---|
| 2005/0226370 A1* | 10/2005 | Al-khalidy | A61B 6/466 378/27 |
| 2008/0092225 A1 | 4/2008 | Nieuwenhuis | |
| 2008/0224061 A1* | 9/2008 | Smith | G01T 1/1647 250/394 |
| 2009/0092225 A1* | 4/2009 | Boese | A61B 6/504 378/19 |
| 2010/0195792 A1* | 8/2010 | Kunz | A61B 6/4452 378/65 |
| 2010/0329534 A1* | 12/2010 | Biermann | A61B 6/4441 378/197 |
| 2011/0150307 A1* | 6/2011 | Souza | G06T 7/0012 382/131 |
| 2016/0278124 A1* | 9/2016 | Zhao | H04W 74/08 |
| 2016/0278724 A1* | 9/2016 | Papaioannou | A61B 6/102 |
| 2020/0253567 A1* | 8/2020 | Ghazi | A61B 6/032 |

OTHER PUBLICATIONS

Miroshnychenko, Sergil & Khobta, Yurii & Nevgasymyi, Andrii & Senchurov, Sergil & Miroshnychenko, Oleksandra & Radko, Dmytro. (2020). Using tomosynthesis for detection of pneumonia caused by COVID-19. DOI: 10.13140/RG.2.2.23921.43363. [retrieved Sep. 9, 2021] Retrieved from the Internet. <https://www.researchgate.net/publication/340460503_Using_tomosynthesis_for_detection_of_pneumonia_caused_by_COVID-19>.

Gothlin, Jan & Gajer, Mais, (2013). The Utility of Digital Linear Tomosynthesis Imaging of Total Hip Joint Arthroplasty with Suspicion of Loosening: A Prospective Study in 40 Patients. BioMed research international. 2013. 594631. DOI: 10.1155/2013/594631. [retrieved Sep. 9, 2021] Retrieved from the Internet. >https://www.researchgate.net/publication/257207016_The_Utility_of_Digital_Linear_Tomosynthesis_Imaging_of_Total_Hip_Joint_Arthroplasty_with_Suspicion_of_Loosening_A_Prospective_Study_in_40_Patients.

Vedantham, Stinivasan & Karellas, Andrew & Vijayaraghavan, Gopal & Kopans, Daniel (2015). Digital Breast Tomosynthesis: State of the Art. Radiology. 277. 663-684. 10.1148/radiol.2015141303. [retrieved Sep. 9, 2021] Retrieved from the Internet. <https://www.researchgate.net/publication/284705971_Digital_Breast_Tomosynthesis_State_of_the_Art>.

Stevens GM, Birdwell RL, Beaulieu CF, Ikeda DM, Pelc NJ. (abstract) Circular tomosynthesis: potential in imaging of breast and upper cervical spine—preliminary phantom and in vitro study, Radiology. Aug. 2003:228(2):569.75. doi: 10.1148/radiol.2282020295. Epub Jun. 23, 2003. PMID: 12821770. [retrieved Jul. 24, 2023] Retrieved from the Internet. <https://pubs.rsna.org/doi/abs/10.1148/radiol.2282020295?journalCode=radiology>.

A. C. Kak and Malcolm Slaney, (abstract) Principles of Computerized Tomographic Imaging, IEEE Press, 1988. [retrieved Jul. 26, 2023] Retrieved from the Internet. <https://www.osti.gov/biblio/5813672>.

Sidky, Emil & Rose, Sean & Reiser, Ingrid & Pan, Xiaochuan. (2019). (abstract) Filtered back-projection for digital breast tomosynthesis with 20 filtering. 183. DOI: 10.1117/12.2513342, [retrieved Jul. 24, 2023] Retrieved from the Internet. <https://www.spiedigitallibrary.org/conference-proceedings-of-spie/10948/1094851/Filtered-back-projection-for-digital-breast-tomosynthesis-with-2D-filtering/10.1117/12.2513342.short?SSO=1>.

Stevens, Grant & Fahrig, Rebecca & Pelc, Norbert. (2001). (abstract) Filtered back projection for modifying the impulse response of circular tomosynthesis. Medical physics. 28. 372-80. DOI: 10.1118/1,1350588. [retrieved Jul. 24, 2023]. Retrieved from the Internet. <https://pubmed.ncbi.nim.nih.gov/11318319/>.

* cited by examiner

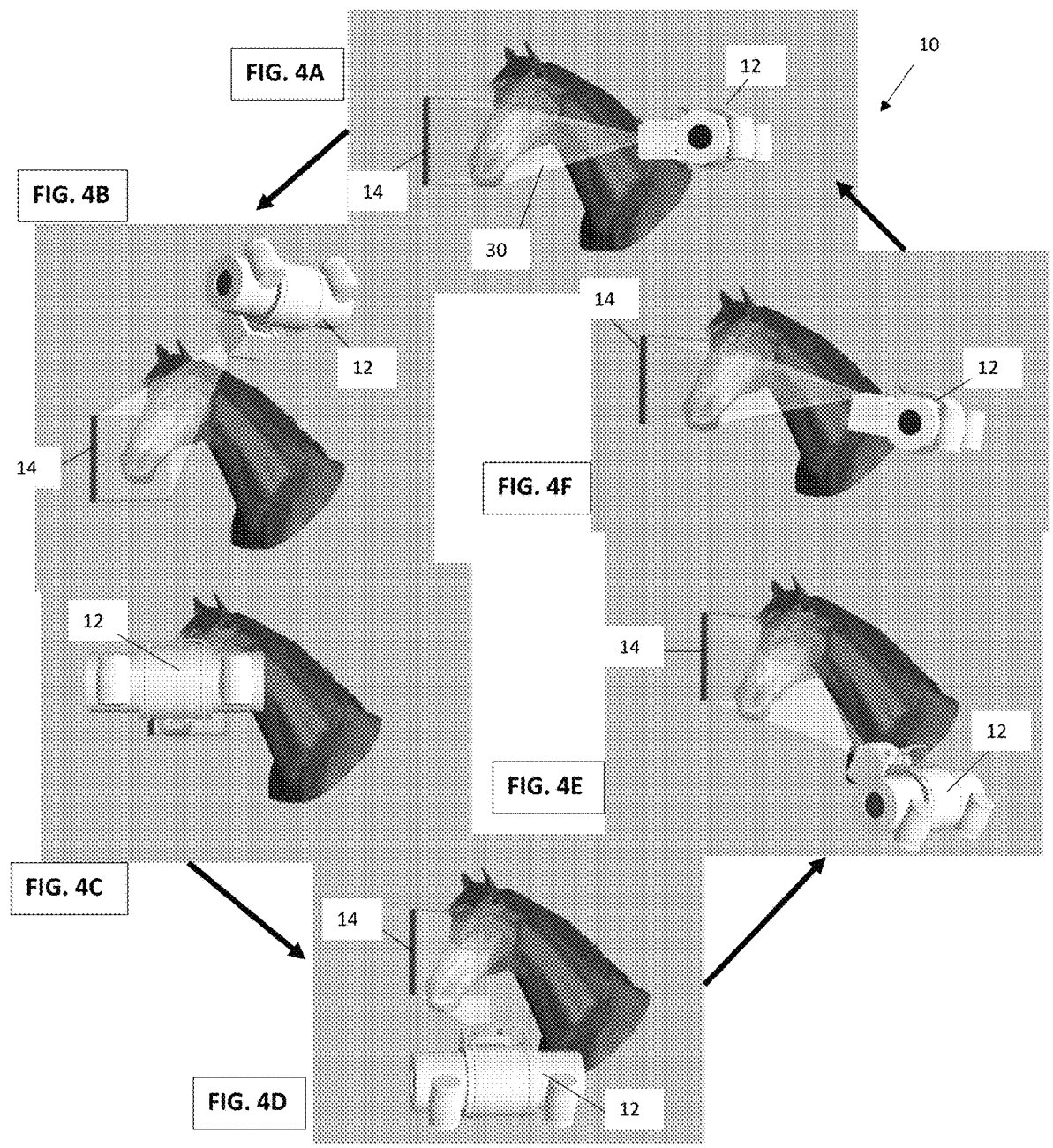

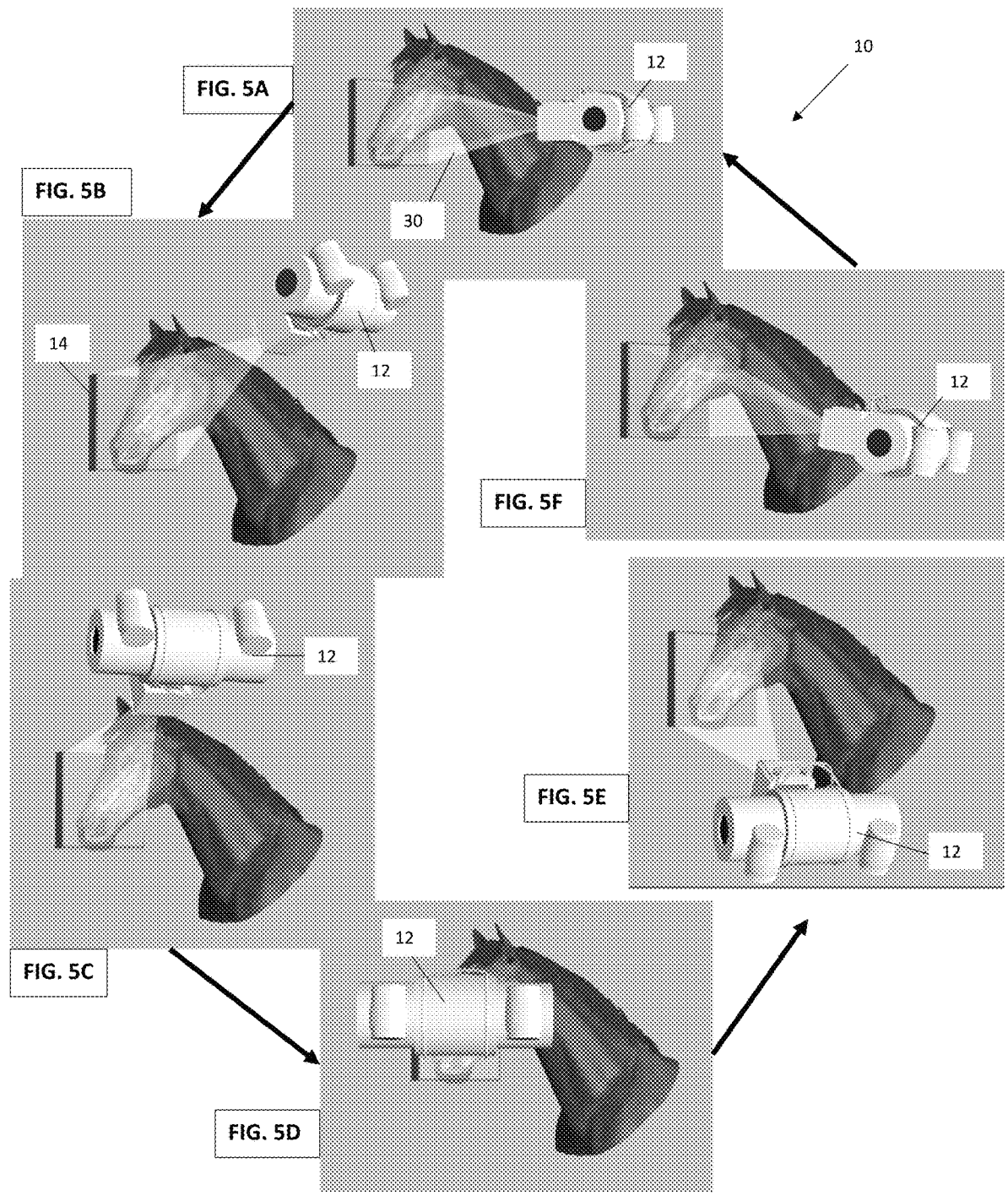

Prior Art – linear scan

Prior Art – linear arc scan

SYSTEM AND METHOD FOR PERFORMING SPIRAL-TRAJECTORY TOMOSYNTHESIS

TECHNICAL FIELD OF THE INVENTION

The present invention relates to tomosynthesis systems and methods. More specifically, the invention relates to spiral-trajectory tomosynthesis.

BACKGROUND OF THE INVENTION

Getting an accurate three-dimensional (3D) X-Ray attenuation map is the ultimate goal of a CT and/or tomosynthesis procedure. As with many ideals, this goal is only partially achievable. The actual result of a tomosynthesis reconstruction is a 3D attenuation map convolved with 3D kernel defined by a scanning trajectory of:

$$T(x, y, z) = \iiint A(x-\xi, y-\eta, z-\zeta) * K(\xi, \eta, \zeta) d\xi\, d\eta\, d\zeta \quad (1)$$

where
- $A(x-\xi, y-\eta, z-\zeta)$ is an attenuation map (ideal 3D image);
- $K(\xi, \eta, \zeta)$, is a 3D convolution kernel defined by a scanning trajectory; and
- $T(x, y, z)$ is the reconstructed and observable tomosynthesis image.

We begin with an assumption that there are two small metal beads located in 3D space having coordinates XYZ= (−1, 0, −1) and XYZ=(+1, 0, +1), and also that the reconstructed tomosynthesis image consists of two layers corresponding to Z=−1 and Z=+1.

In the case of arc-type motion, the reconstructed layers look like the images of FIG. 1A and FIG. 1B. FIG. 1A shows the effect of layer-leaking in the case of arc-type scanning at a depth of Z=−1, while FIG. 1B shows the layer corresponding to a depth of Z=+1.

In the case of circular-type motion, the reconstructed layers look like the images of FIG. 2A and FIG. 2B. These images show the effect of layer-leaking in the case of circular scanning. FIG. 2A illustrates a layer corresponding to a depth of Z=−1 and FIG. 2B corresponds to a layer at a depth of Z=+1.

The "leaked structures" have a smaller contrast but they are still non-desirable artifacts complicating the analysis process, making it heuristic and relying heavily on a doctor's experience. In conventional applications of scanning "sparse" objects (e.g., lung) or "flat" objects (e.g., female breast) the effect is obviously relevant. At the same time there are a lot of techniques and protocols describing the flawed diagnostic process as "error-proof" and "established." On another hand, in applications such as podiatry—where doctors are looking for small bone fractures or ligament tissue characteristics—leaking is more critical and a heavy problem which may cause misdiagnosed cases due to confusing "belonging-to-layer" and "leaked" structures and anatomy details.

Existing Methods of Mitigating Layer-Leaking Effect

As mentioned above, the desired result of any 3D X-Ray imaging technique is getting the accurate attenuation map $(A(x-\xi, y-\eta, z-\zeta))$. Theoretically speaking, one could write the following formula:

$$A(x, y, z) = \iiint T(x-\xi, y-\eta, z-\zeta) * K^{-1}(\xi, \eta, \zeta) d\xi\, d\eta\, d\zeta \quad (2)$$

where
$K^{-1}(\xi, \eta, \zeta)$ is the inversion of the kernel $K(\xi, \eta, \zeta)$.

Unfortunately, this approach cannot be applied exactly as defined in the formula (2) since the inversion problem is ill-conditioned for all practical cases.

There are multiple methods suggested by different authors (see, for example, citations [5] and [6]) regarding practical mitigation of the artifacts caused by convolution (see formula (1)). Such methods can be represented or described by the formula:

$$\tilde{A}(x, y, z) = \iiint T(x-\xi, y-\eta, z-\zeta) * C(\xi, \eta, \zeta) d\xi\, d\eta\, d\zeta \quad (3)$$

where,
- $\tilde{A}(x, y, z)$ is an observable tomosynthesis image; and
- $C(\xi, \eta, \zeta)$ is an additional convolution kernel defining a correctional algorithm.

The common drawback of these methods is that they do not remove or even mitigate the layer leaking artifact. They just "re-shape" it.

Until the invention of the present application, these and other problems in the prior art went either unnoticed or unsolved by those skilled in the art. The present invention provides both system and methods for spiral-trajectory tomosynthesis which are capable of performing multiple functions without sacrificing important analytical features.

SUMMARY OF THE INVENTION

There is disclosed herein an improved system and method for tomosynthesis scanning which avoids the disadvantages of prior systems and methods while affording additional structural and operating advantages.

Generally speaking, the tomosynthesis scanning system comprises an X-ray emitter connected to a first robotic device, and an X-ray detector connected to a second robotic device. The first robotic device moves the emitter along a first spiral trajectory path and, optionally, the second robotic device moves the detector along a second spiral trajectory path during the scanning process. Where both the emitter and detector move, the movement is synchronized. A computer is used to control the first and second robotic devices.

In specific embodiments of the system, the first spiral trajectory path is at least 360 degrees. In other specific embodiments, the second spiral trajectory path is also at least 360 degrees.

In specific embodiments, the first spiral trajectory path is at least 720 degrees. In other specific embodiments, the second spiral trajectory path is also at least 720 degrees.

With respect to operation of the disclosed tomosynthesis scanning system, generally speaking the method comprises placing an object to be scanned between an X-ray emitter and an X-ray detector, moving the X-ray emitter along a first spiral path while emitting a photon beam at the X-ray detector, allowing the photon beam to pass through the object before reaching the X-ray detector, measuring attenuation of the photon beam reaching the X-ray detector, and producing an image based on the measured attenuation of the photon beam.

In optional embodiments of the method, moving the X-ray detector during the scanning process is also a feature. Preferably, the X-ray detector moves along a second spiral path, wherein the second spiral path is synchronized with the first spiral path.

These and other aspects of the invention may be understood more readily from the following description and the appended drawings.

BRIEF DESCRIPTION OF THE DRAWINGS AND APPENDICES

For the purpose of facilitating an understanding of the subject matter sought to be protected, there are illustrated in the accompanying drawings and appendices, embodiments thereof, from an inspection of which, when considered in connection with the following description, the subject matter sought to be protected, its construction and operation, and many of its advantages should be readily understood and appreciated.

FIGS. 4A through 4F are a sequence of six images illustrating an embodiment of a spiral trajectory tomosynthesis system in different positions as it scans using both a moving source and a moving detector;

FIGS. 5A through 5F are a sequence of six images illustrating an embodiment of a spiral trajectory tomosynthesis system in different positions as it scans using a moving source and a fixed or stationary detector;

DETAILED DESCRIPTION OF THE INVENTION

Figure 1B:
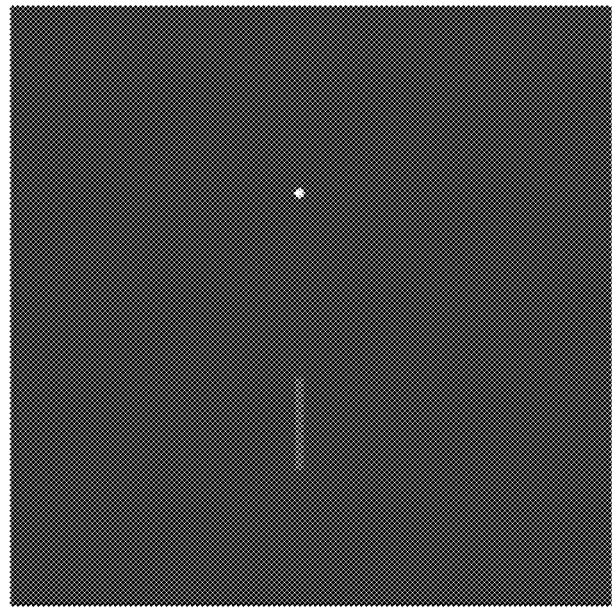
FIGS. 1A and 1B are separate images showing layer-leaking in arc-type scanning process at a depth of Z=−1 and Z=+1, respectively.
Figure 1A:
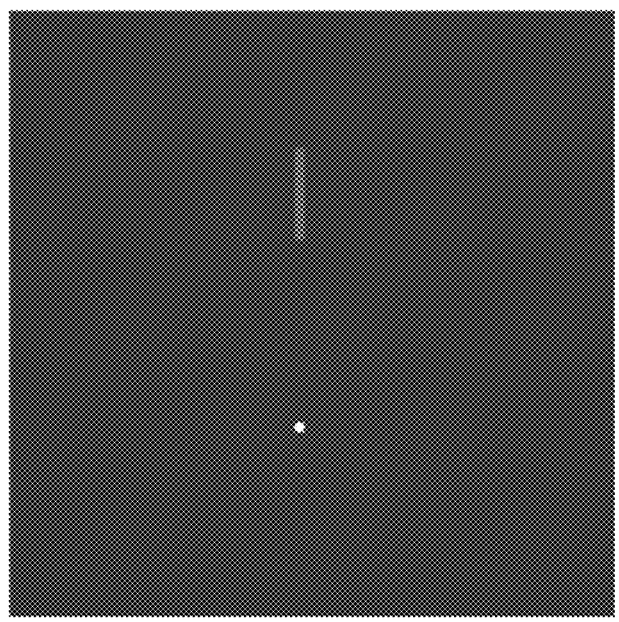
Figure 2B:
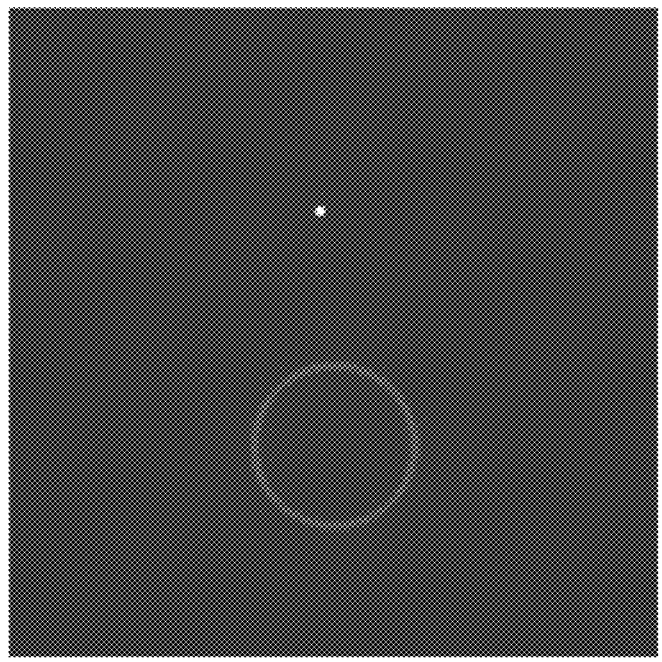
FIGS. 2A and 2B are separate images showing layer-leaking in a circular-type scanning process at a depth of Z=−1 and Z=+1, respectively.
Figure 2A:
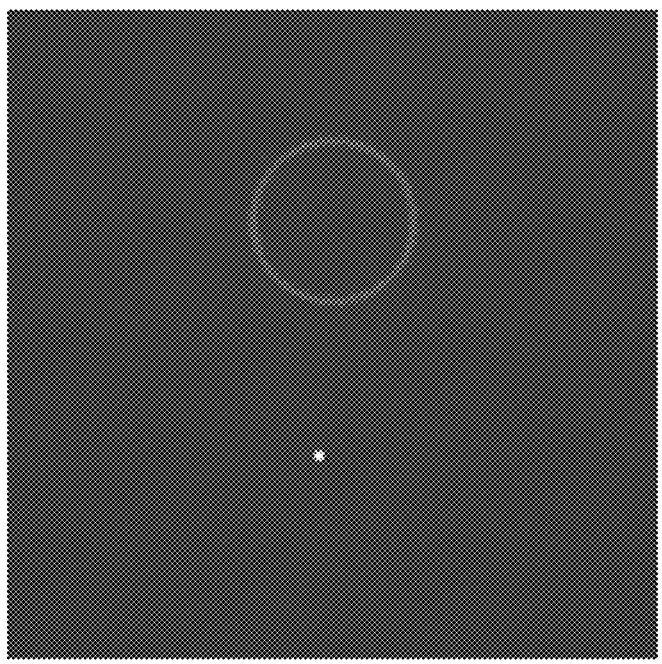

While this invention is susceptible of embodiments in many different forms, there is shown in the drawings and will herein be described in detail at least one preferred embodiment of the invention with the understanding that the present disclosure is to be considered as an exemplification of the principles of the invention and is not intended to limit the broad aspect of the invention to any of the specific embodiments illustrated.

Figure 3A:
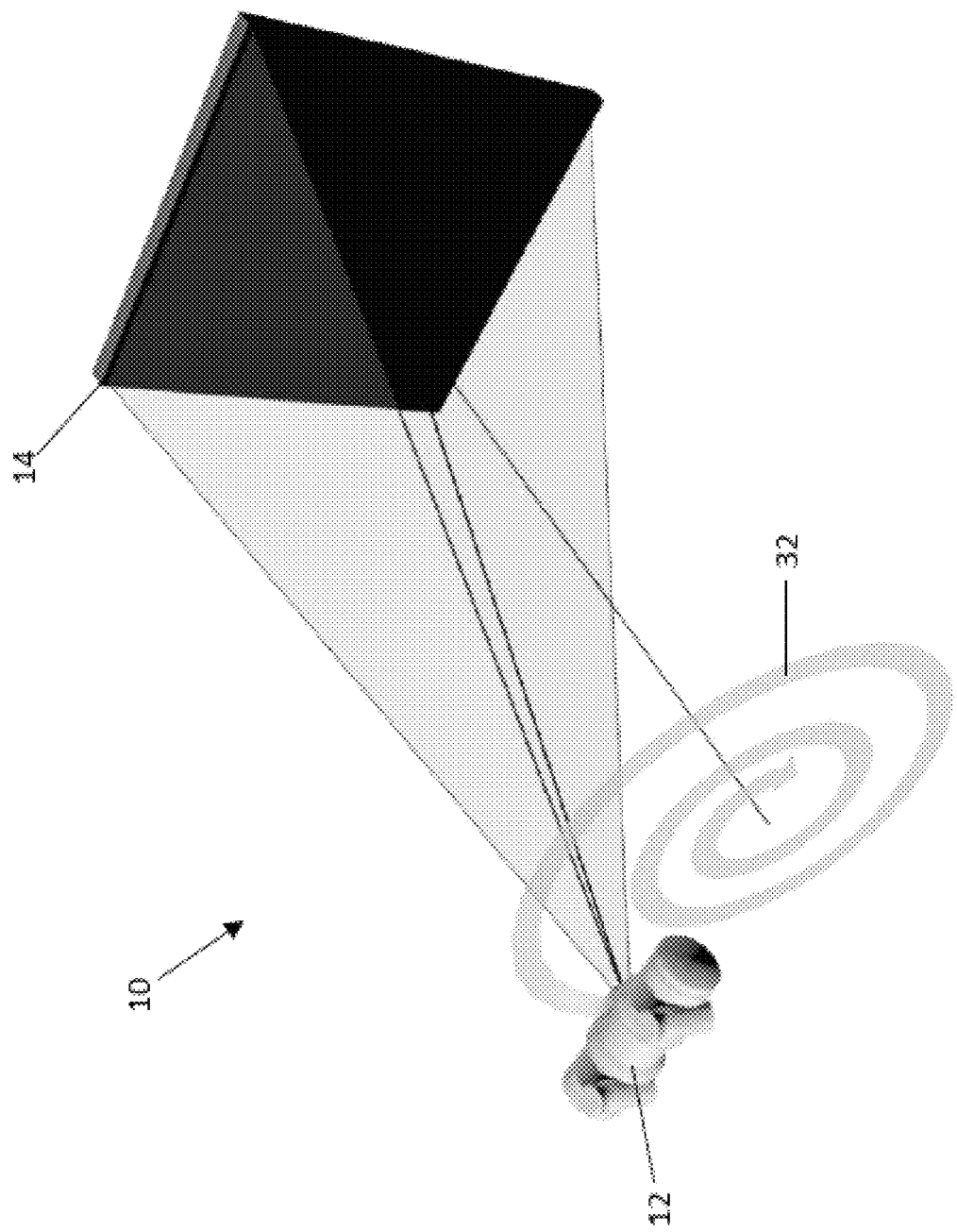
FIG. 3 is an illustration of an embodiment of a spiral-trajectory tomosynthesis showing the emitter moving while the detector is fixed.
Figure 3B:
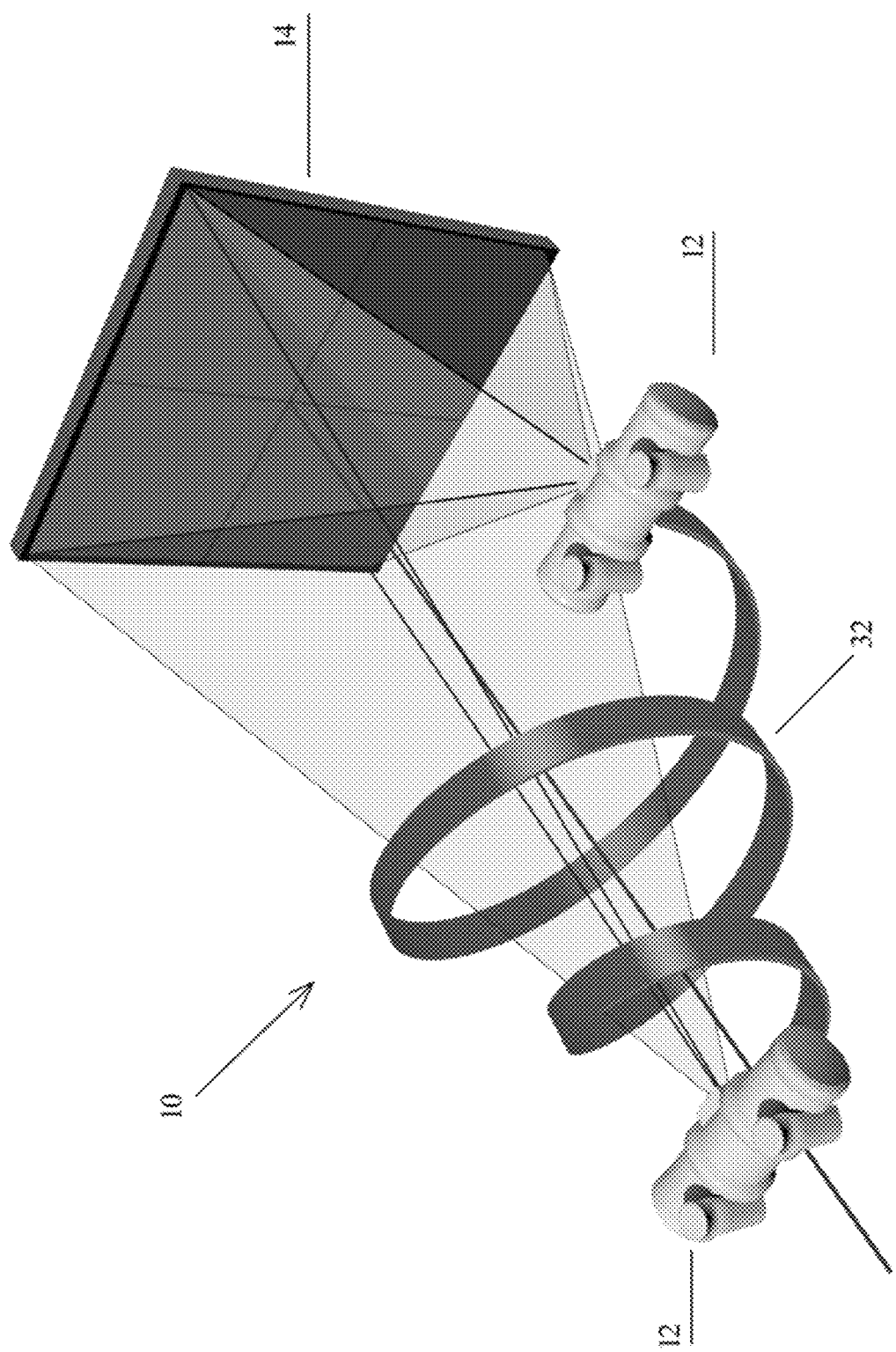
Figure 3C:
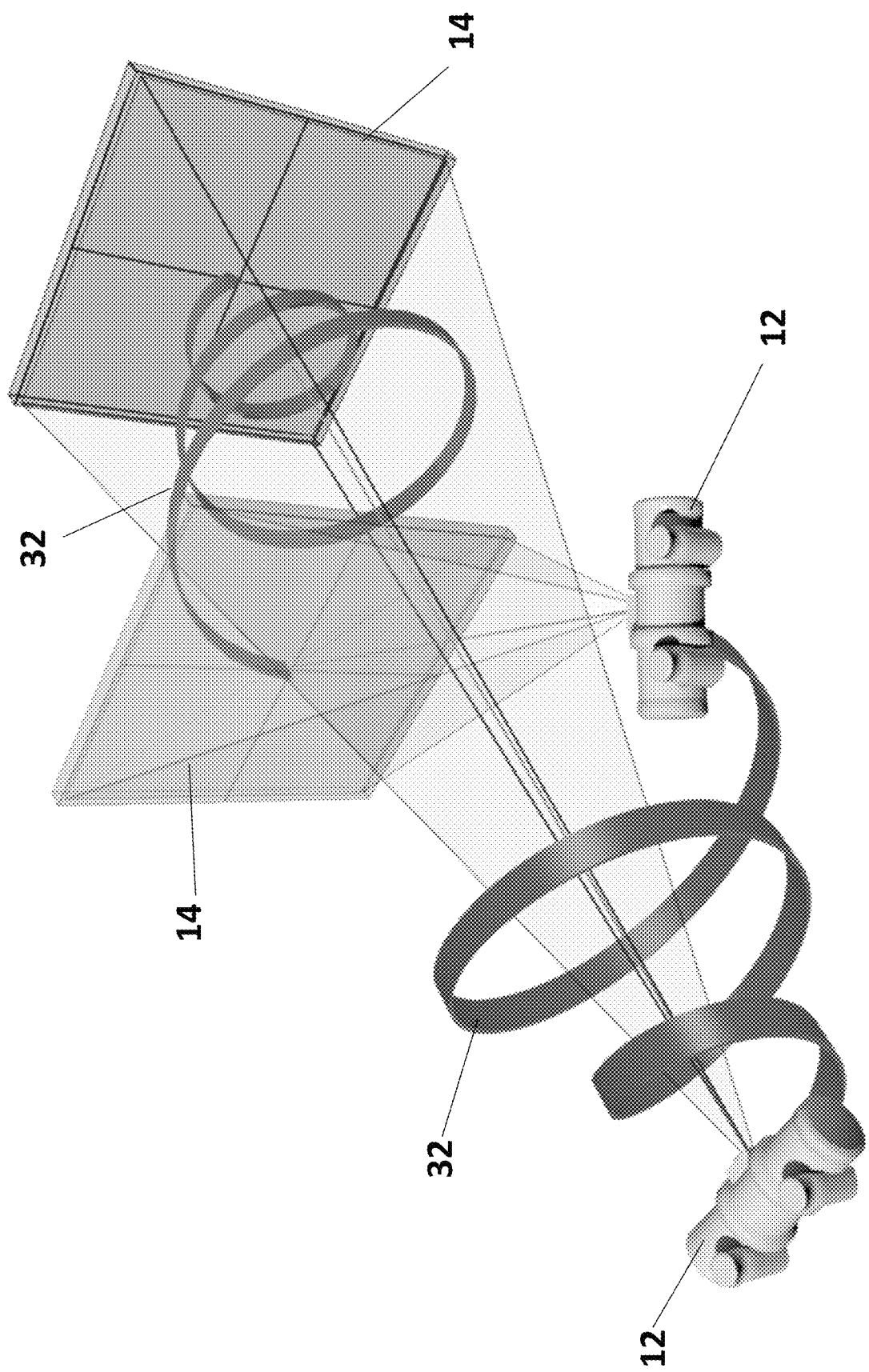
Figure 6:
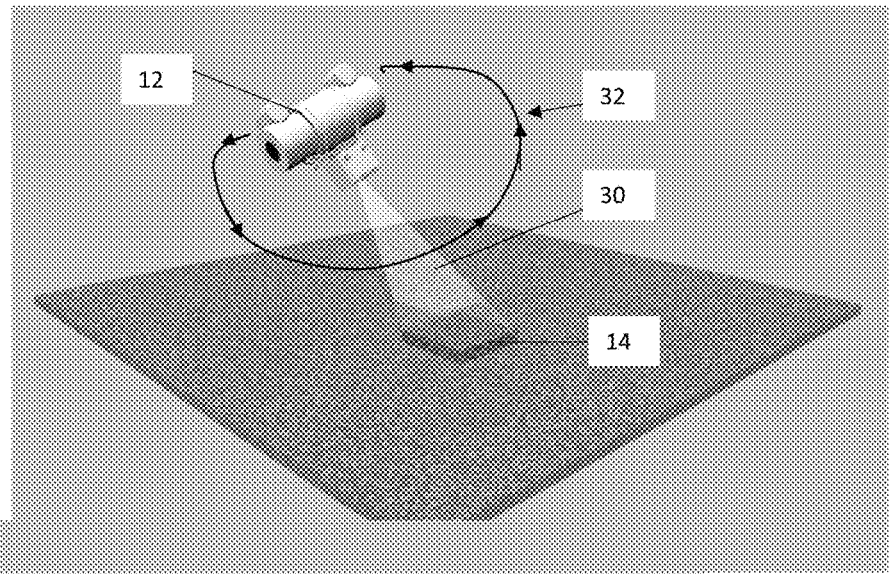
FIGS. 6-13 illustrate movement of a source emitter following a path indicated by the arrows of FIG. 6.
Figure 7:
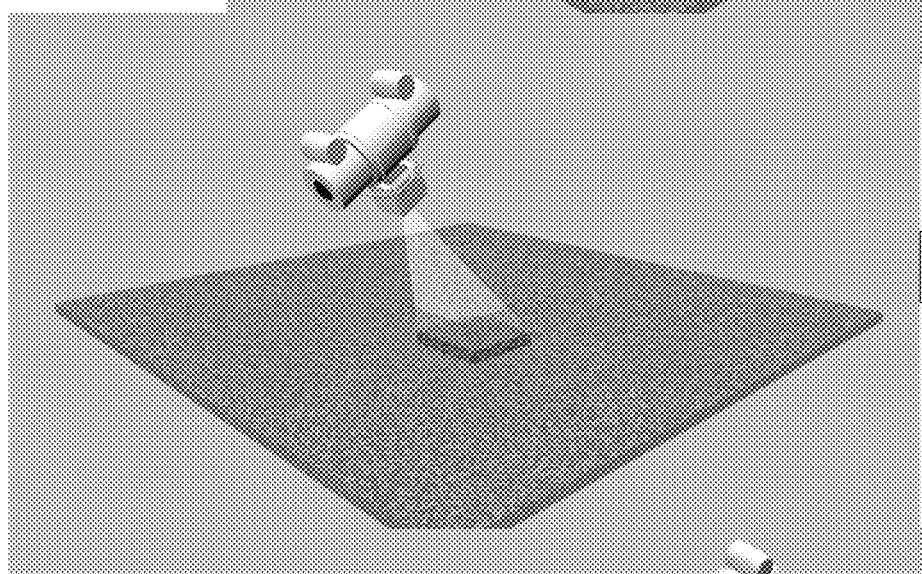
Figure 8:
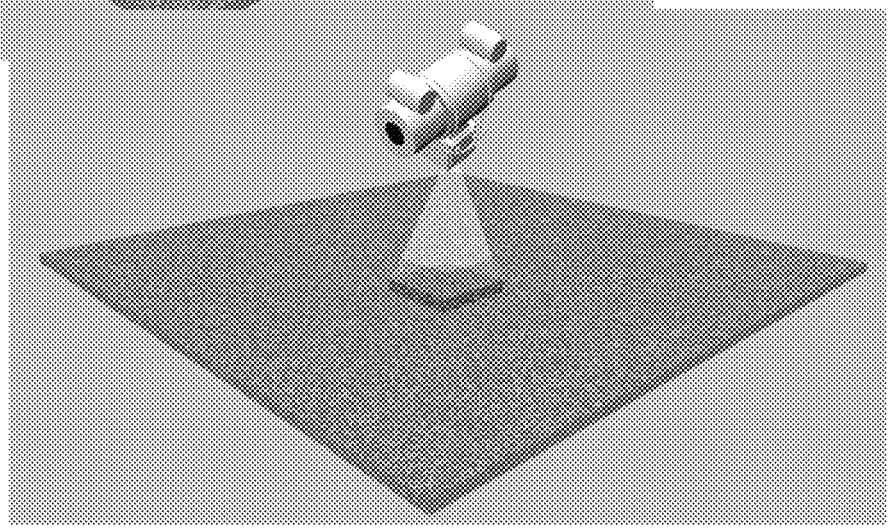
Figure 9:
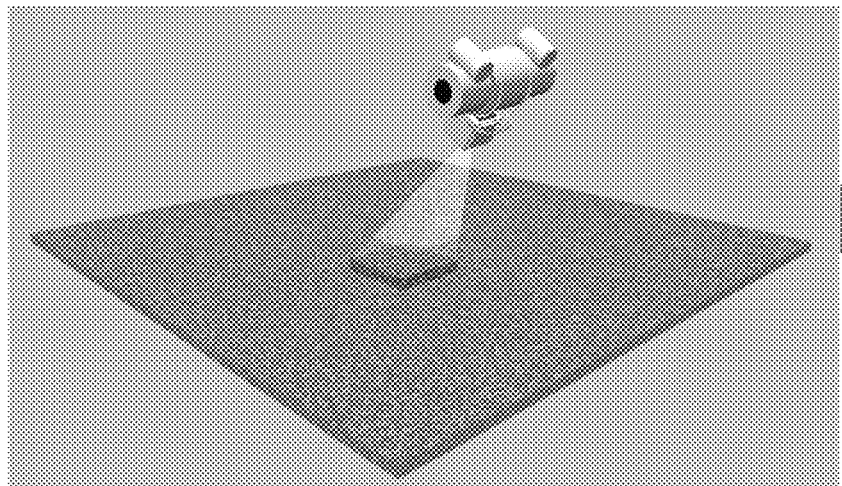
Figure 10:
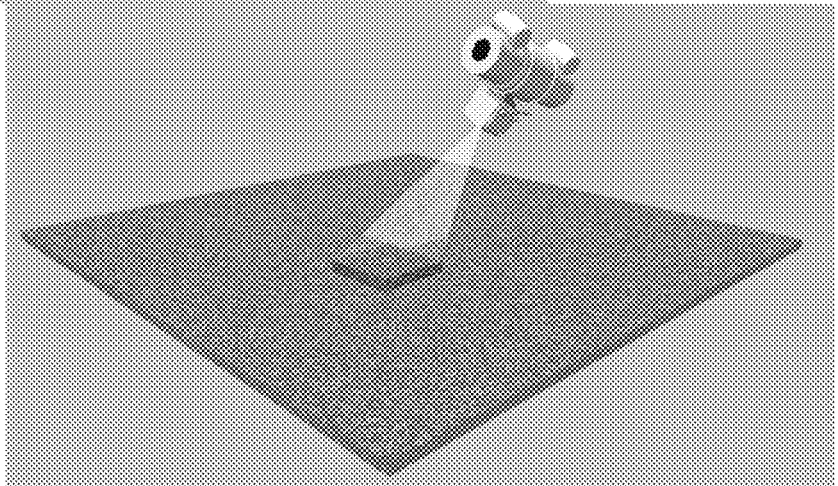
Figure 11:
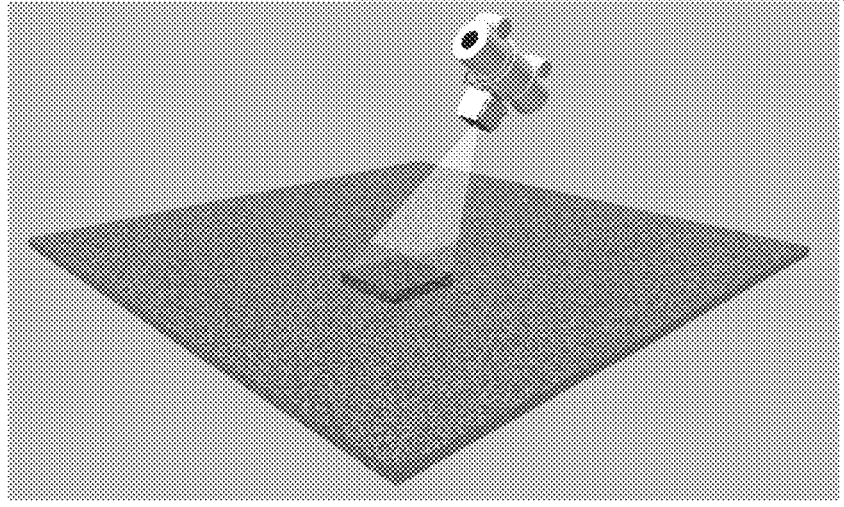
Figure 12:
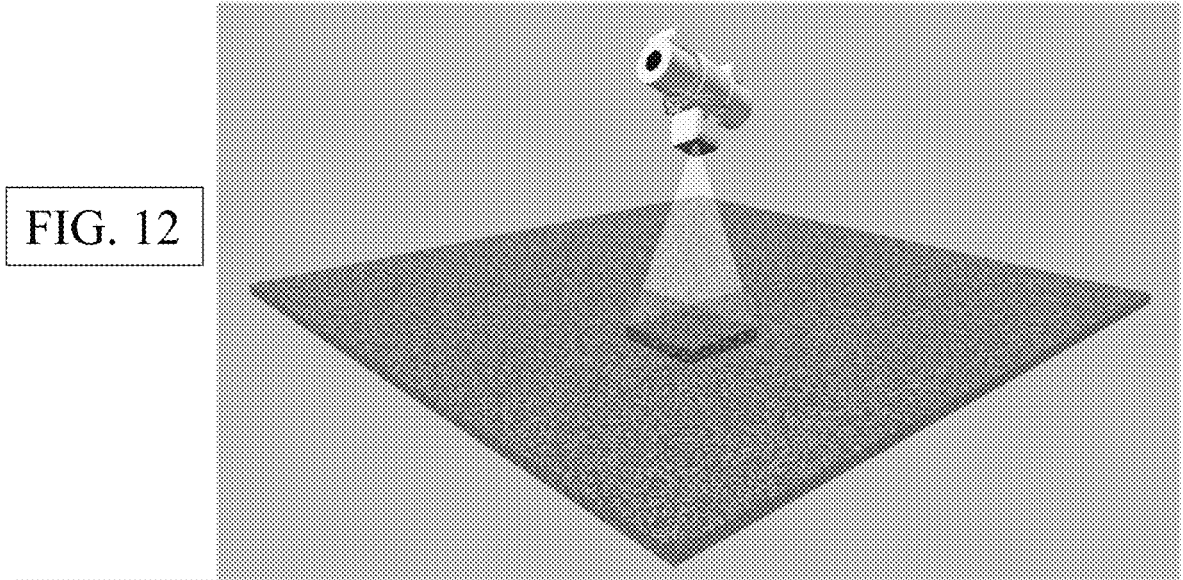
Figure 13:
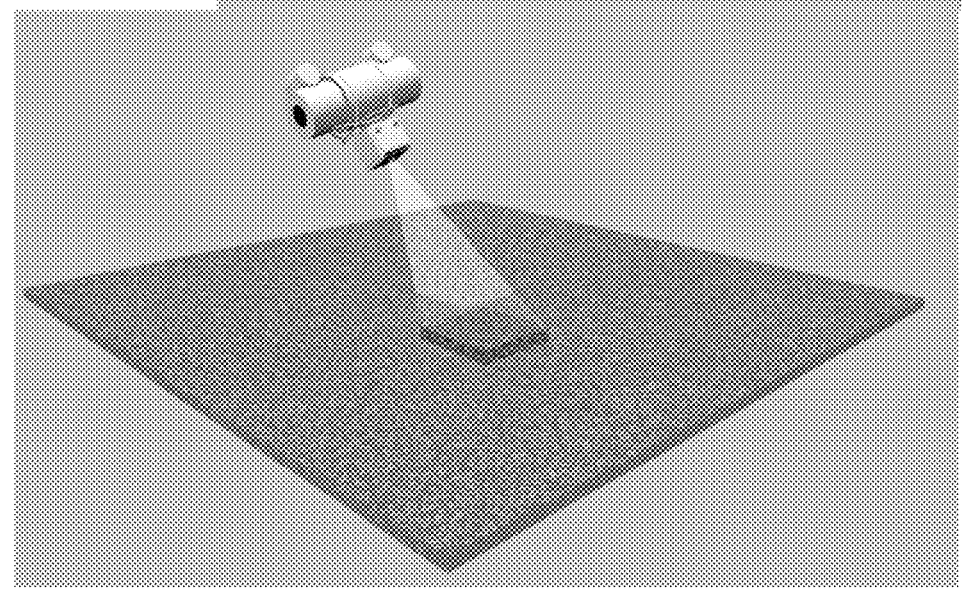

Generally speaking, as shown in FIGS. 3A, 3B, and 3C, the disclosed system 10 contains an X-Ray source 12 (also referred to as an emitter herein), and an X-Ray detector 14, for scanning sample (object) 20. The X-Ray source 12 and X-Ray detector 14 may both move in a complex motion or the X-Ray detector 14 may remain stationary during the scanning process. The system 10 is controlled by a computer 16 which transfers data from the detector 14 to a computer storage 18 and then uses the stored data to prepare a tomosynthesis reconstruction, as described below.

Referring to FIGS. 4-24, there is illustrated embodiments of the spiral-trajectory tomosynthesis system 10, as well as corresponding methods. The particular illustrated embodiments are for use with humans, animals and inanimate objects (e.g., circuit boards). In fact, one of the advantages of the system and method disclosed herein is for efficient and accurate detection of COVID-19 in human patients. However, it should be understood that the principles of the invention can be more broadly applied to many other purposes using the unique scanning system and technique.

An X-Ray detector is an electronic device capable of converting a cumulative energy of photons hitting a detector element (also called a pixel) within a given time (also called the accumulation time) into a digital value. Pixels are arranged as two-dimensional (2D) regular rectangular structures. An X-Ray Source (or emitter) is the source of an X-Ray photon beam 30.

As shown in FIGS. 4A through 4F, an embodiment of the system 10 incorporates an emitter 12 moving in a first spiral, while the detector 14 moves in a synchronized second spiral. Similarly, FIGS. 5A through 5F illustrate an embodiment where only the emitter 12 is moving in a spiral, while the detector 14 maintains a fixed position. The spiral path 32 of the emitter 12 is further illustrated in FIGS. 6-13. Spiral movement is defined as winding in a continuous and gradually widening (or tightening) curve, either around a central point on a flat plane or about an axis so as to form a cone.

Conversely, FIGS. 29-35 illustrate a linear scanning movement where the object, placed on a conveyor, is moved through a scanning area. This technique would be similar to moving the emitter in a straight line over the fixed object. The system illustrated in FIGS. 36-47 moves in an arc during scanning. These systems have been found to be inferior to the spiral-trajectory scanning of the present system 10.

X-Ray attenuation is a measure of the reduction in the X-Ray photon beam intensity. That is, when the X-Ray photon beam 30 penetrates a material, the number of photons coming out from material without changing direction or being absorbed is smaller than the number of photons before penetration. Inside the material, X-Ray photons get scattered and absorbed due to various physical effects. The ratio between the number of photons (i.e., intensity) before and after penetration of the object is called attenuation. The attenuation value depends on photon energy and material. For example, one centimeter of water has an attenuation value of approximately 1.2 when the photon energy is ~80 kVp. This means that the "after-object" photon amount is a factor of 1.2 smaller than the "before-object" photon amount. Attenuation as a physical factor has special scales (i.e., is mapped to special scales) called CT numbers or Hounsfield units (HU).

A three-dimensional X-Ray attenuation map is a 3-D image. Every element (typically called a "voxel") of such an image has a value equal to the X-Ray attenuation factor of the material located at a particular point in space (voxel).

The scanning process involves the emission and detection of photons before and after penetration of a material or object. During a spiral-trajectory scanning process, the X-Ray source 12 and detector 14 move under the following conditions: X-Ray source 12 is always positioned in such a way that when the emitted photons penetrate a sample (called a scanned object) they are then hitting the detector 14. The scanned object gets completely or partially exposed during every detector accumulation cycle. After every accumulating cycle, the computer 16 reads a digital signal from the detector 14 and writes it to the computer storage (e.g., hard drive) 18 as a file, also called an input projection or input view. Typically (in most commercial tomosynthesis systems) the detector 14 remains fixed, and the X-Ray emitter 12 moves along either a straight line (see, for example, citation no. [1]), an arc (see, for example, citation no. [2]) or a circle (see, for example, citations nos. [3, 6]).

A tomosynthesis image is a set of radiograph-type images which are also called layers. Every layer contains a sharp (i.e., in-focus) image or cross-section of the object within a limited range of depth. The sharp (in-focus) layer is superimposed with blurry (i.e., not in focus) images corresponding to other object depth ranges. So, every tomosynthesis layer image contains sharp (in-focus) details located at a specific depth and blurry (out-of-focus) details located at other depths of the scanned object. Such superimposition of blurry details is called "layer leaking".

Tomosynthesis reconstruction is a conversion from a set of two-dimensional views (projections) into a set of two-dimensional images (also called layers). The theory and practical implementation of this conversion (reconstruction) is known to those skilled in the art and within the public domain (see, for example, citation no. [4]).

A preferred embodiment of the presently disclosed system 10 includes an X-Ray detector 14, an X-Ray Source (emitter) 12 and mechanical unit(s) 26 used to move the emitter 12 and (optionally) the detector 14 relative to each other. As previously noted, the system 10 is controlled by a computer 16, which transfers data from the detector 14 to storage 18 and then uses the data, via a specific processing algorithm, for reconstruction (i.e., spiral tomosynthesis reconstruction, see below). The mechanical unit(s) 26 can be specially designed or can be modified "off-the-shelf" industrial robots.

Using a preferred embodiment of the system 10, during a scanning process:
- the emitter 12 moves along a flat spiral trajectory of 360+ degrees (typically 720 degrees or 2 full revolutions);
- the emitter 12 is always positioned in such a way that when the emitted photons penetrate a sample (called a scanned object) they then hit the detector 14;
- the detector 14 is either stationary or it moves synchronically with the emitter 12 where the detector center trajectory is also spiral;
- the detector 14 always (at any moment) is positioned in such a way that a symmetry axis of the emitted beam comes through a physical center of the detector 14;
- the scanned object gets completely or partially exposed during every detector accumulation cycle.

The spiral motion of the emitter/source 12 for the system 10 is illustrated in FIG. 3. There is an initial assumption that the reconstruction algorithm is based on a known/conventional approach. It could be, for example, filtered back-projecting (see, for example, citation no. [4]).

The reconstruction process for the present system 10 consists of three steps, with an optional fourth step. Step 1 is performing a tomosynthesis reconstruction process from an entire ensemble of projections. The result is a 3-D tomosynthesis image $S_{full}$. Step 2 is to perform the tomosynthesis reconstruction process from the projections (input views) corresponding to 360-degree coverage and acquired at the start of the spiral trajectory. In the case of 720-degree scanning it is the first half of the trajectory. The result is 3D tomosynthesis image $S_1$. Finally, Step 3 requires performing the tomosynthesis reconstruction process from the projections (input views) corresponding to 360-degree coverage and acquired at the end of the spiral trajectory. In the case of 720-degree scanning it is the last half of the trajectory. The result is 3D tomosynthesis image $S_2$. Optionally, with a 720-degree scan, Step 4 requires getting a final reconstruction result $S_{cleaned}$ by the formula:

$$S_{cleaned} = S_1 + S_2 - S_{full} \quad (4)$$

The theory behind formula (4) is as follows:
If a reconstructed layer is represented as:

$$L_{observed} = L_{clean} + A_{leak} \quad (5)$$

where
  $L_{clean}$ is a 2D attenuation map of the objects located within this layer (in-focus objects);
  $A_{leak}$ is the contribution of the objects, which are "leaking from other layers".

Then, for images obtained as a result of Steps 1-3 described above, it can be written:

$$L_{observed,step1} = L_{clean,step1} + A_{leak,step1}$$

$$L_{observed,step2} = L_{clean,step2} + A_{leak,step2}$$

$$L_{observed,step3} = L_{clean,step3} + A_{leak,step3}$$

$$A_{leak,step1} = A_{leak,step2} + A_{leak,step3} \quad (6)$$

If it is assumed that $L_{clean,step1}$ is approximately equal to $L_{clean,step2}$ which is approximately equal to $L_{clean,step3}$ (formula (7)), then the solution of the linear system equation (6) produces the formula (4) for $L_{clean}$.

As stated below, the formula (7) is the only approximation. It is fair to assume that the reconstructed method listed above as Steps 1-4 provides a mitigation of the layer-leaking effect but not its complete removal.

Consider the goal of distinguishing the content of the current layer and the content "leaked from other layers". In order to accomplish this goal, it is suggested visualizing images acquired on Steps 1-3 side-by-side or one under another with the possibility of switching between these views. This approach gives a person providing image analysis (e.g., radiologist) an idea about "real" and "leaked" content in the observed layer by noting differences between these pictures—i.e., "real content" stays basically the same, while "leaks" change significantly.

With reference to FIGS. 14-28, a specific use for the disclosed system 10 is illustrated. As described in the paper titled "The Concept of the X-ray Apparatus with Tomosynthesis for Thorax Screening" (DOI: 10.13140/RG.2.2.22682.06082) by S. Miroshnychenko, A. Nevgasymyi, O. Miroshnychenko, S. Gouzeev, and B. Goldberg and in the paper titled "Using Tomosysthesis for Detection of Pneumonia caused by COVID-19"(DOI:10.13140/RG.2.2.23921.43363) by S. Miroshnychenko, A. Nevgasimyi, O. Miroshnychenko, Y. Khobta, S. Senchurov, D. Radko and I. Olena, an embodiment of the disclosed system 10 may be used in safely screening patients. The contents of these two articles are hereby incorporated by reference.

Figure 14:
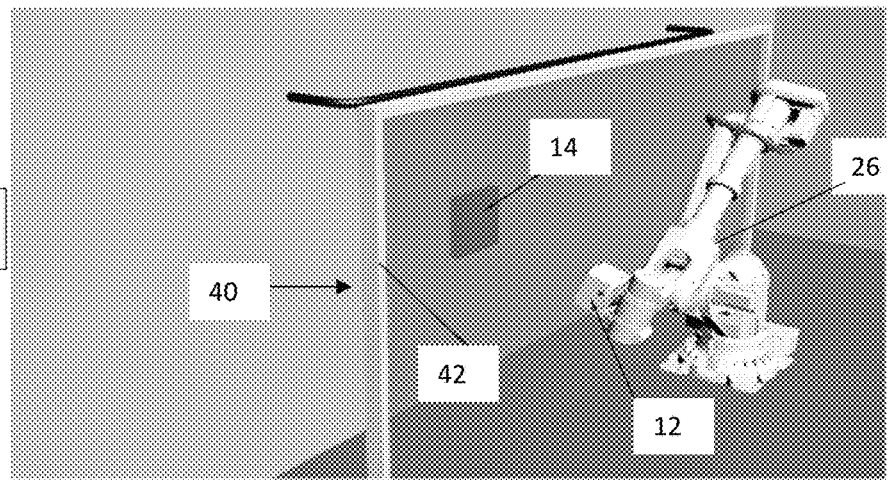
FIG. 14 is a perspective view of an embodiment of a screening site using a shielded area and an embodiment of a spiral-trajectory tomosynthesis machine.
Figure 15:
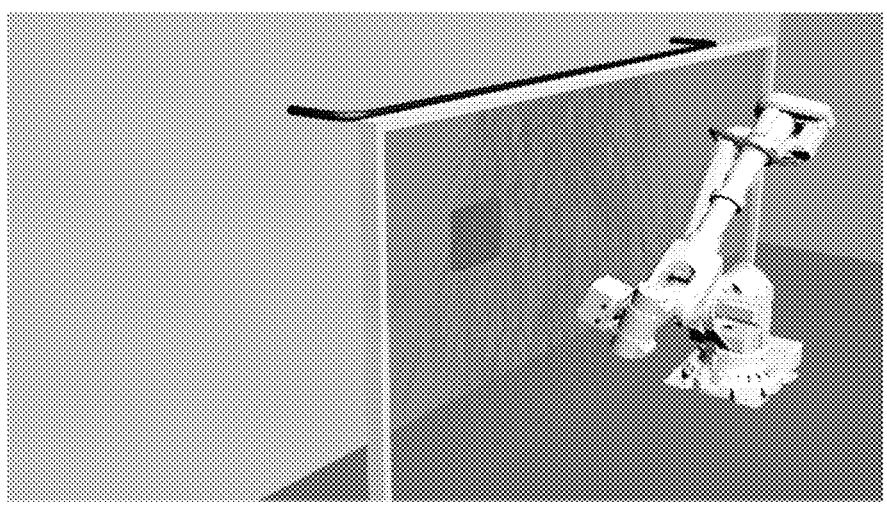
FIG. 15 is a perspective view illustrating disinfecting of the shielded area of FIG. 14.
Figure 16:
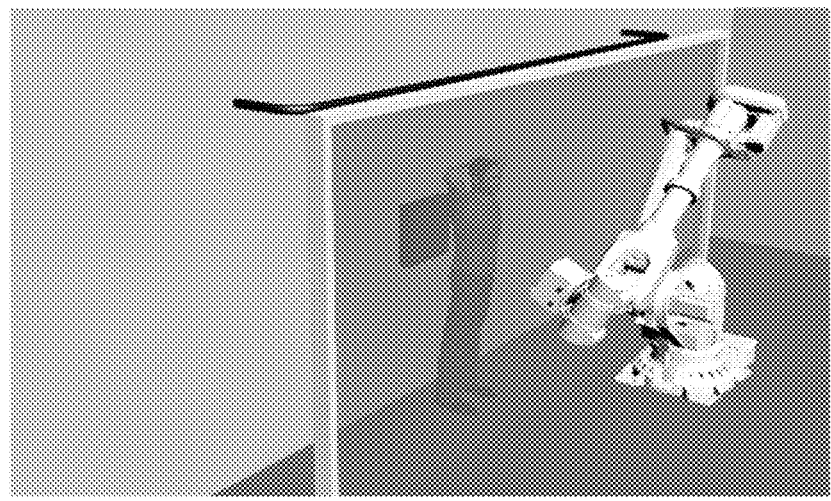
FIG. 16 is an image showing a first patient positioned within the shielded area of FIG. 14.
Figure 17:
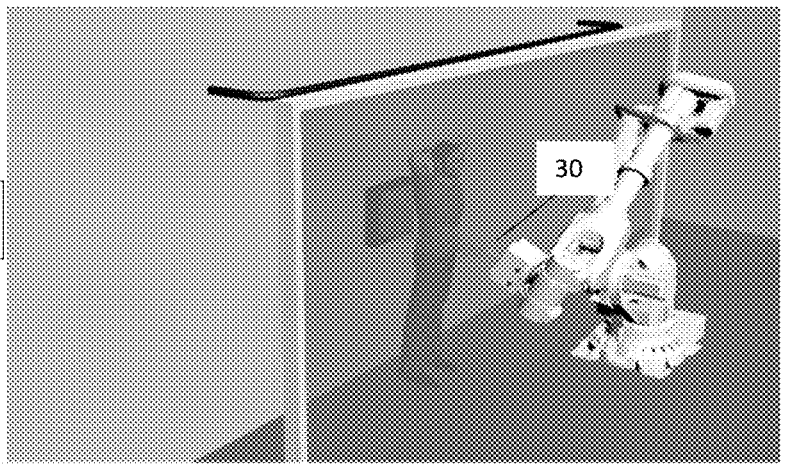
FIGS. 17-20 are images in a sequence to illustrate a spiral-trajectory tomosynthesis scan of the first patient of FIG. 16.
Figure 18:
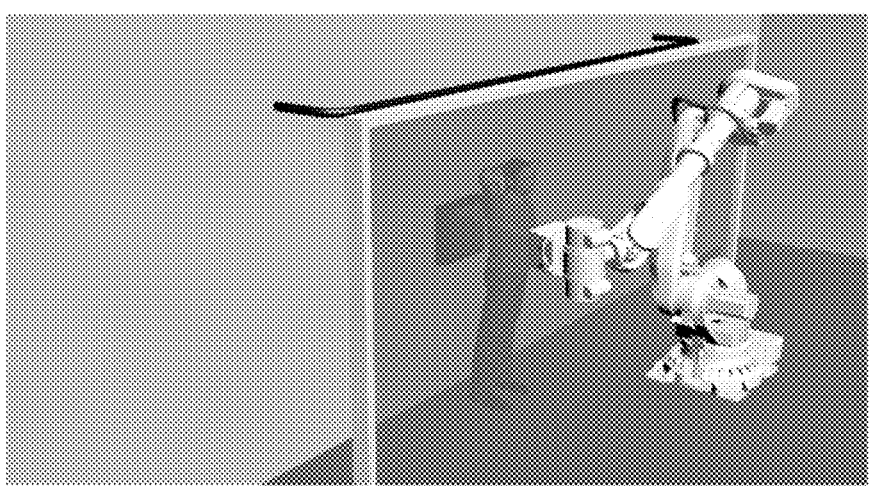
Figure 19:
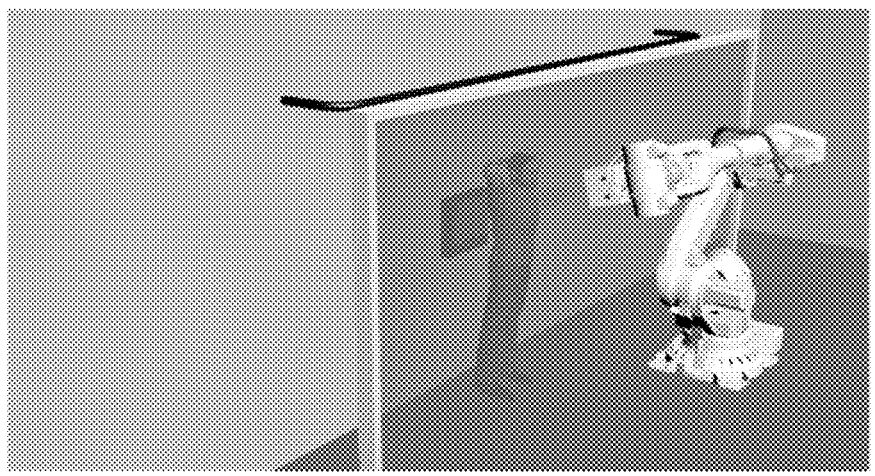
Figure 20:
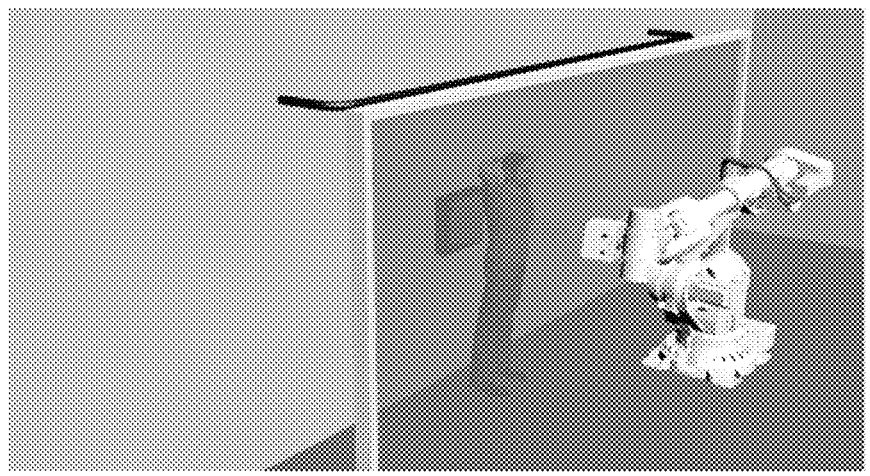
Figure 21:
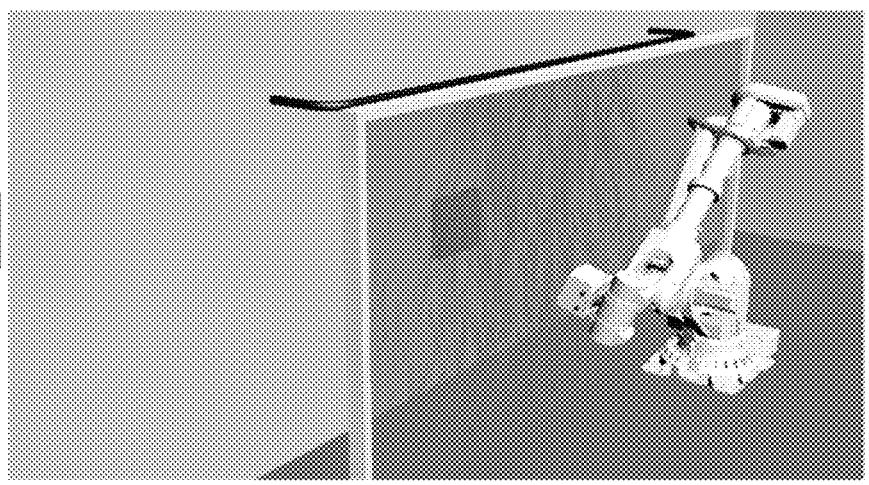
FIG. 21 is an image illustrating disinfecting of the shield area of FIG. 14, much like the image of FIG. 15.
Figure 22:
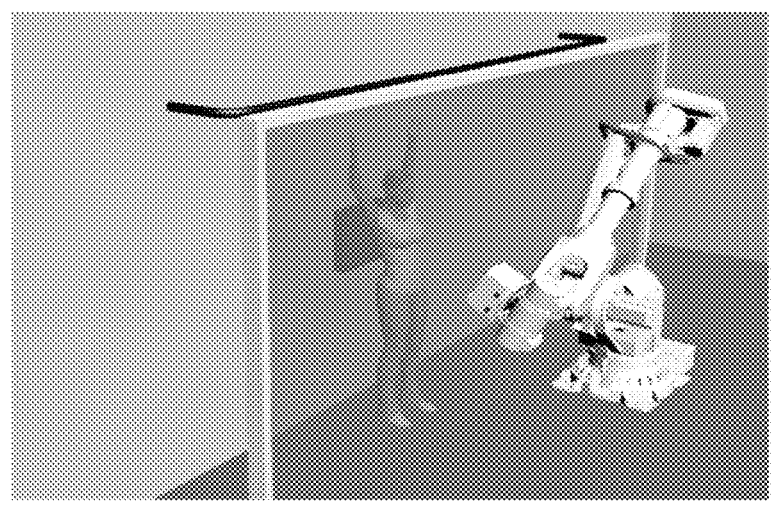
FIG. 22 is an image showing a second patient positioned within the shielded area of FIG. 14.
Figure 23:
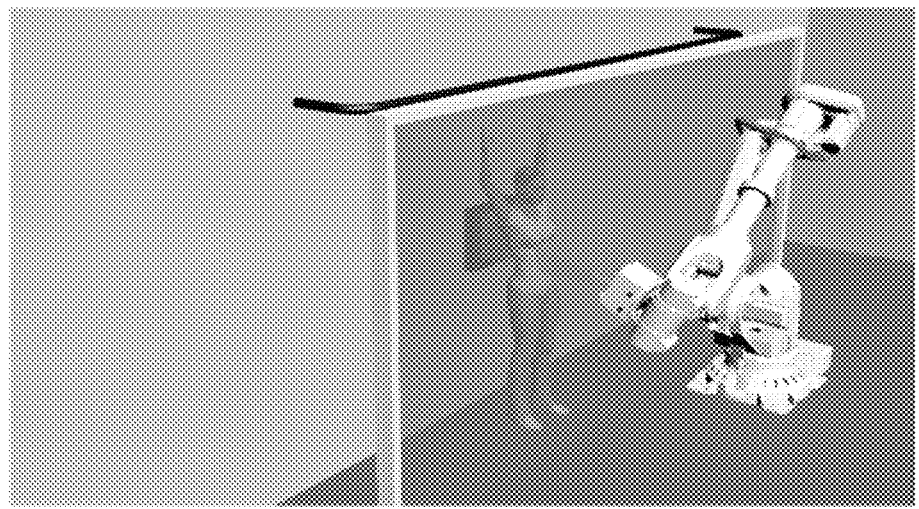
FIGS. 23-27 are images in a sequence to illustrate a spiral-trajectory tomosynthesis scan of the second patient of FIG. 22.
Figure 24:
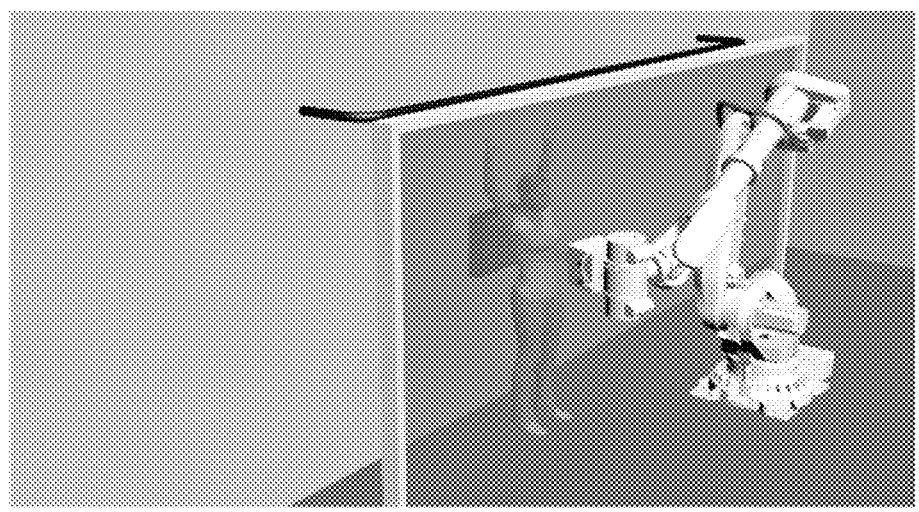
Figure 25:
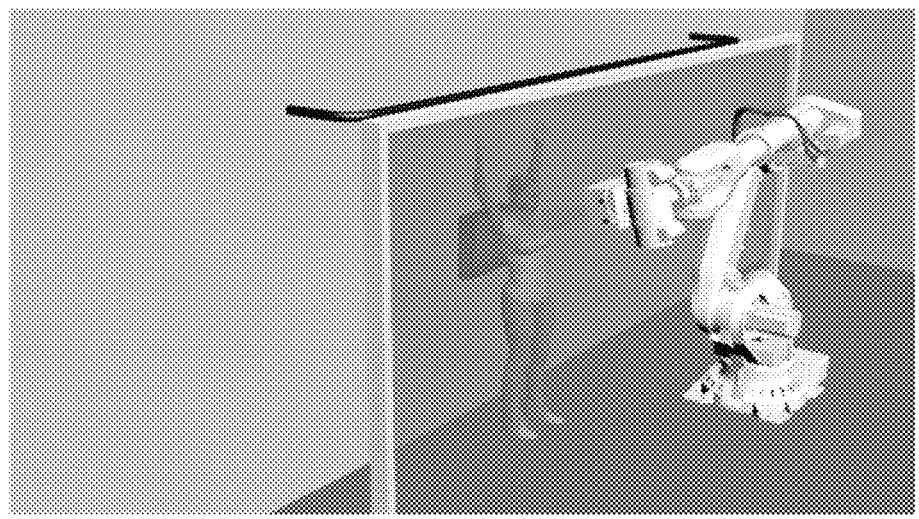
Figure 26:
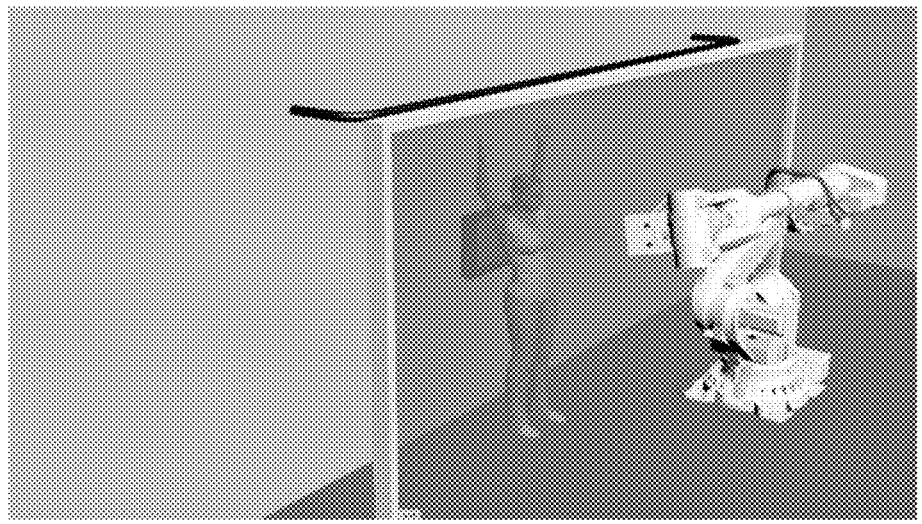
Figure 27:
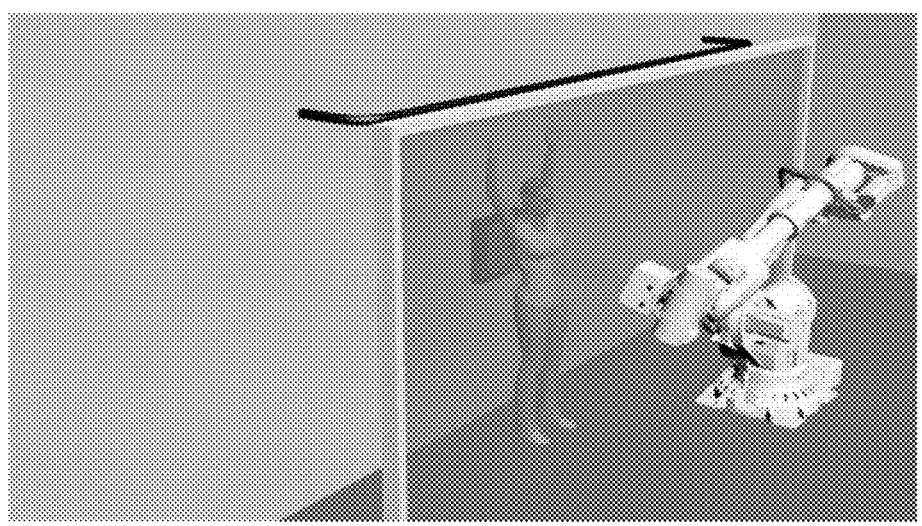
Figure 28:
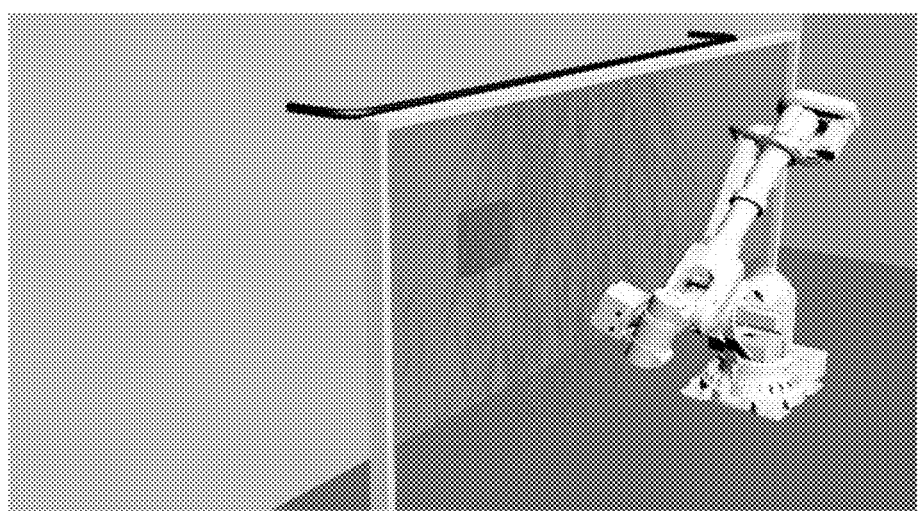
FIG. 28 is an image showing a third disinfecting step of the shielded area of FIG. 14, much like FIGS. 15 and 21.
Figure 29:
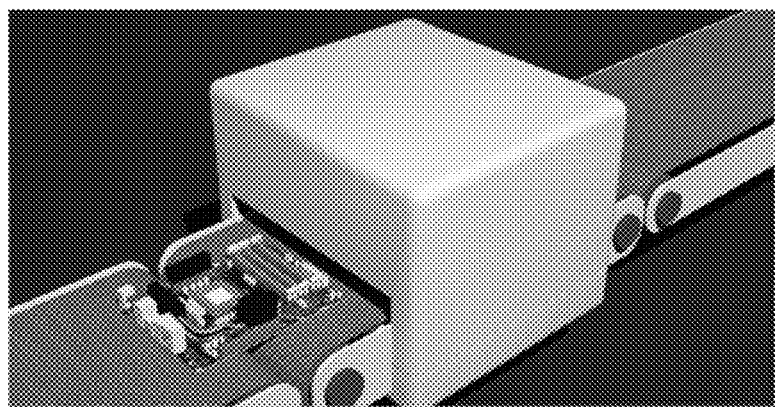
FIGS. 29-35 are a sequence of images illustrating the use of a linear tomosynthesis scanning system and method for scanning electronic circuit boards.
Figure 30:
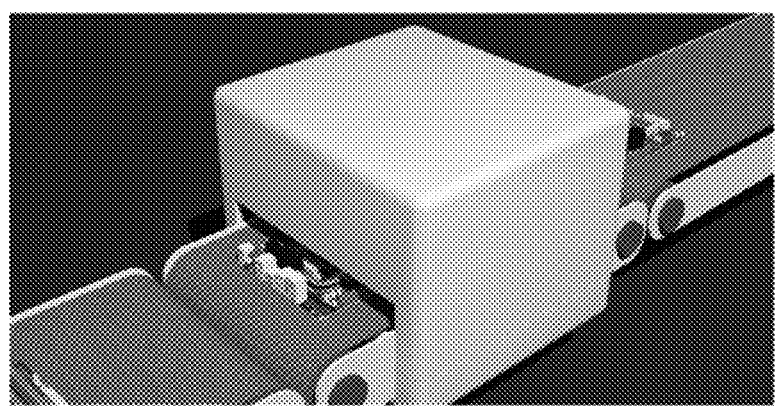
Figure 31:
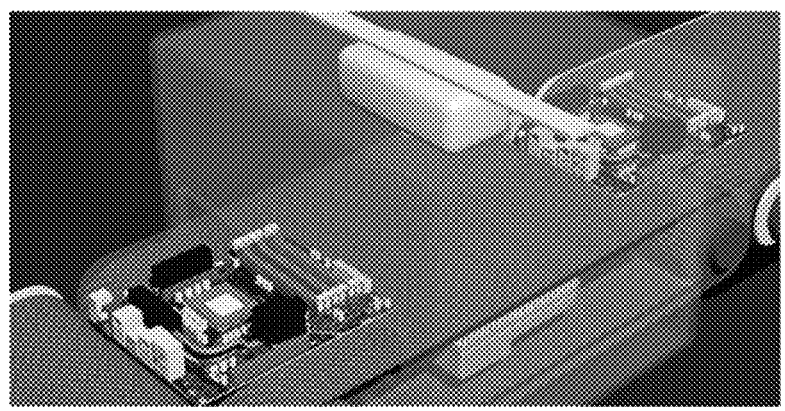
Figure 32:
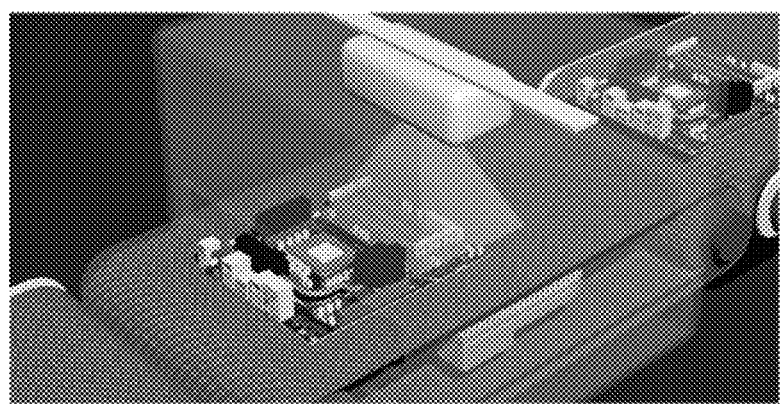
Figure 33:
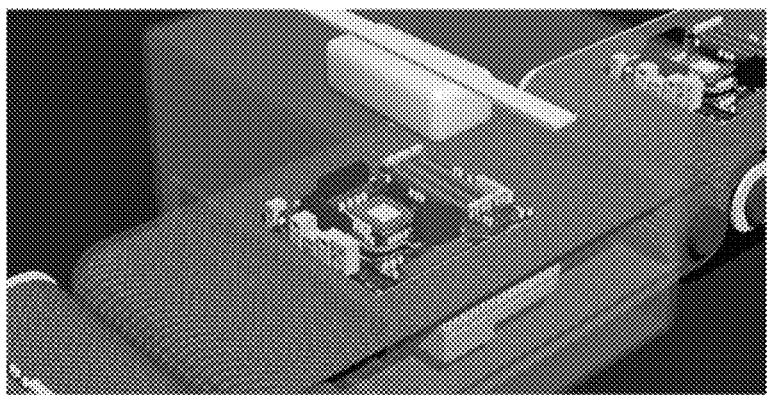
Figure 34:
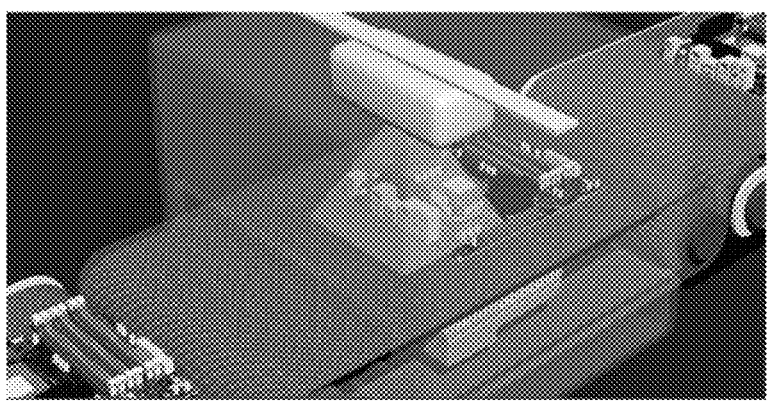
Figure 35:
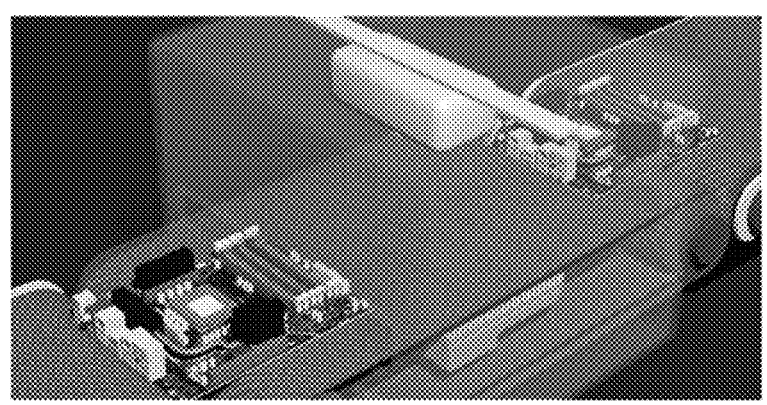
Figure 36:
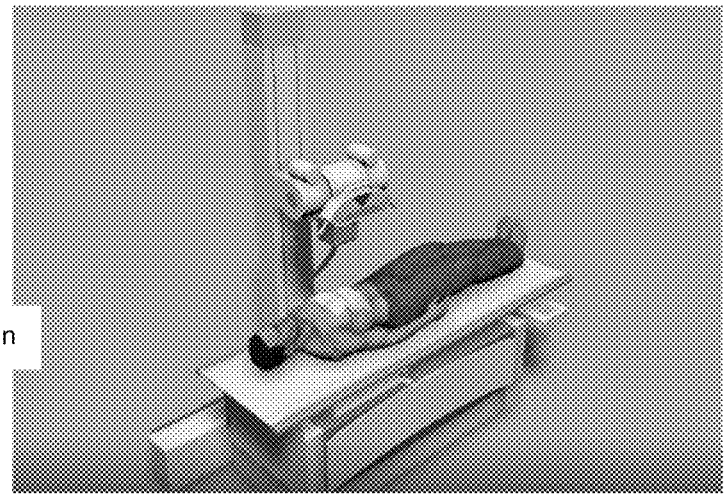
FIGS. 36-47 are a sequence of images illustrating a linear tomosynthesis system and method for scanning the chest and abdominal areas of a patient.
Figure 37:
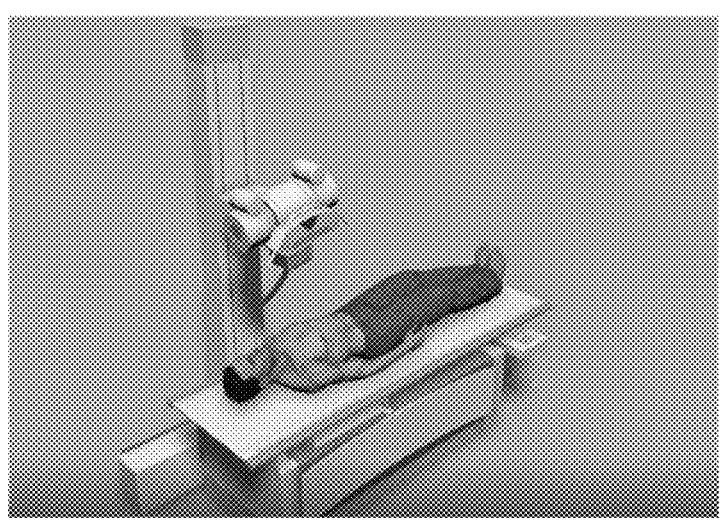
Figure 38:
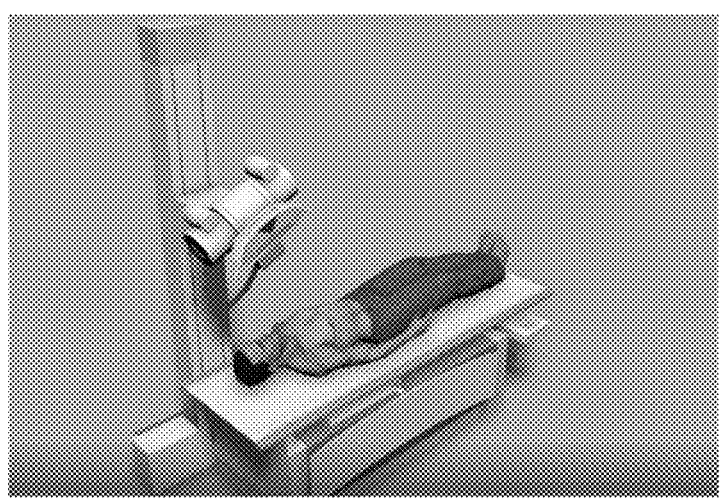
Figure 39:
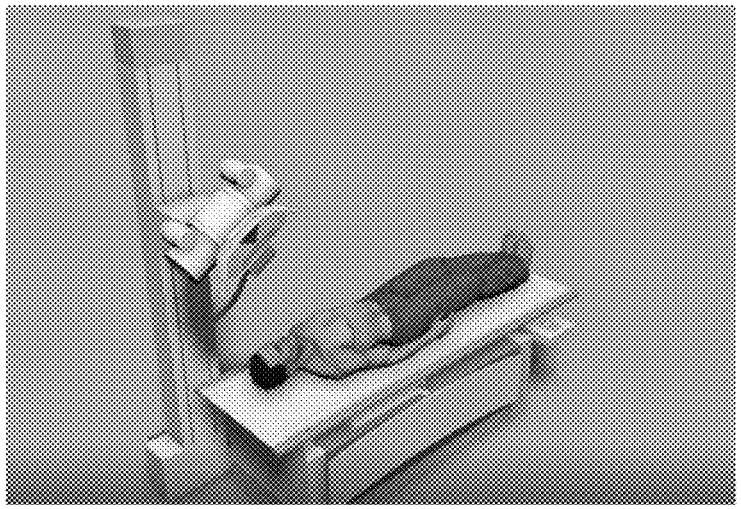
Figure 40:
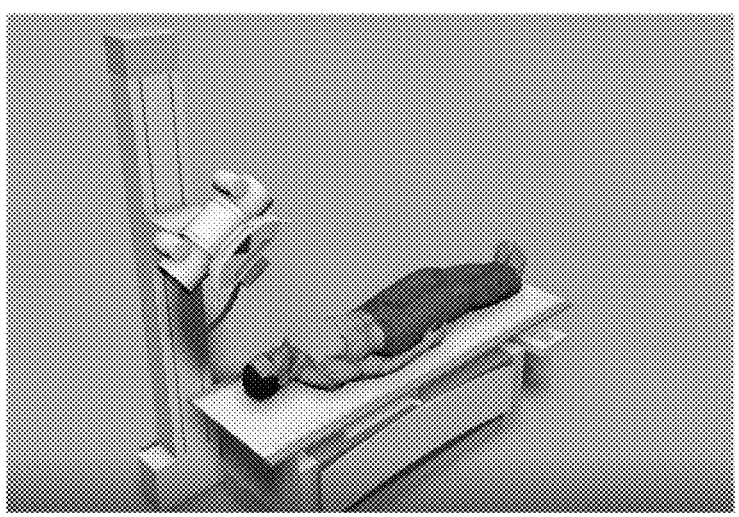
Figure 41:
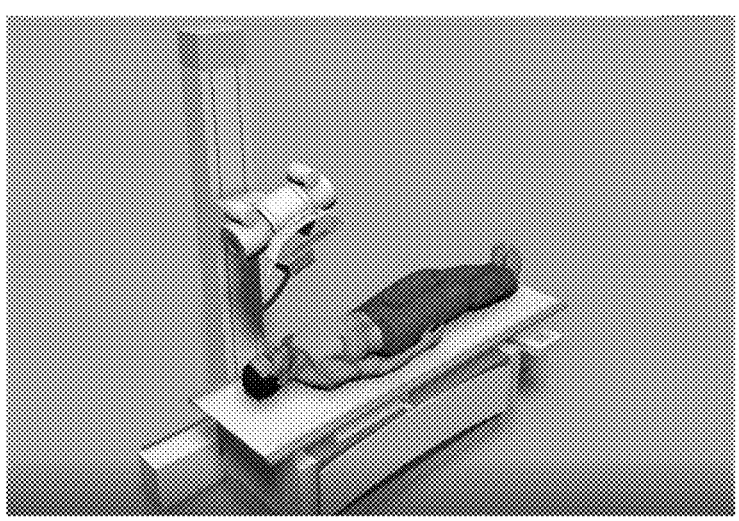
Figure 42:
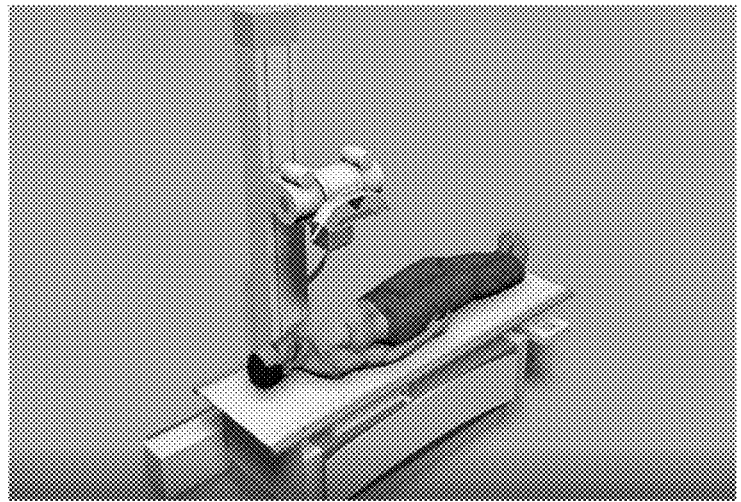
Figure 43:
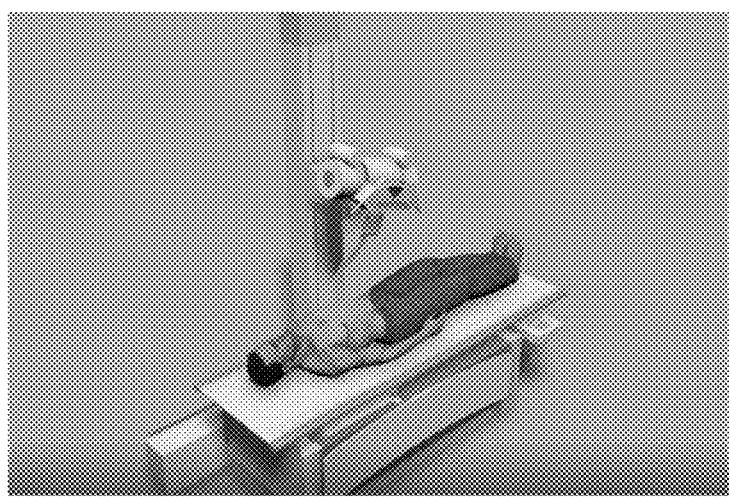
Figure 44:
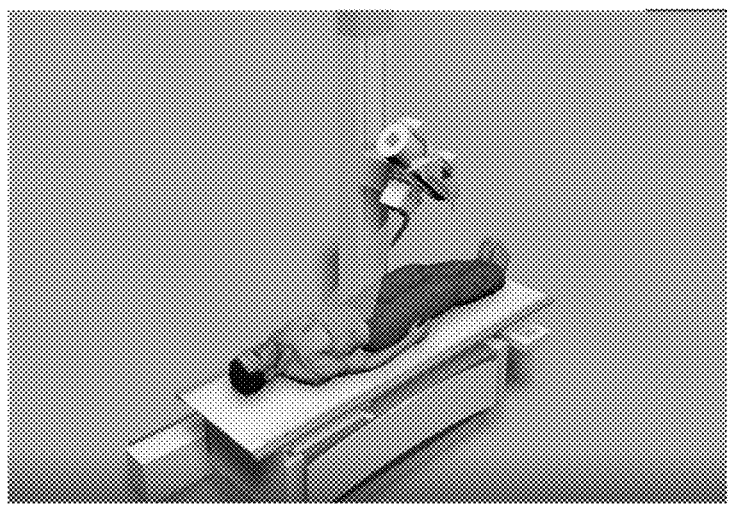
Figure 45:
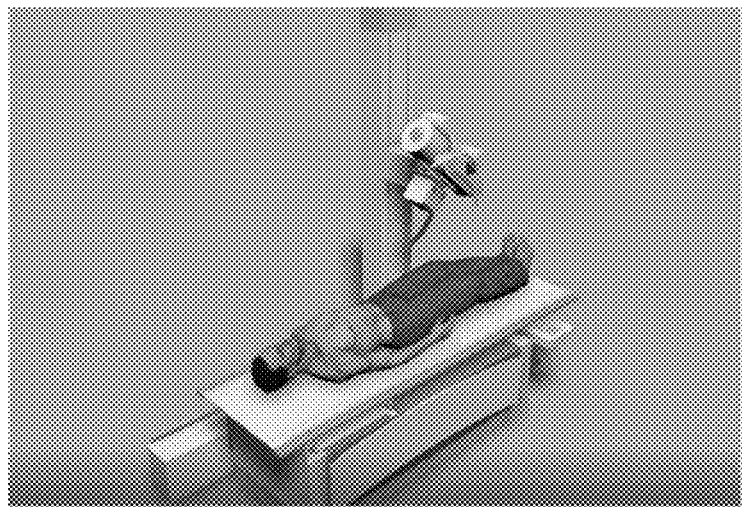
Figure 46:
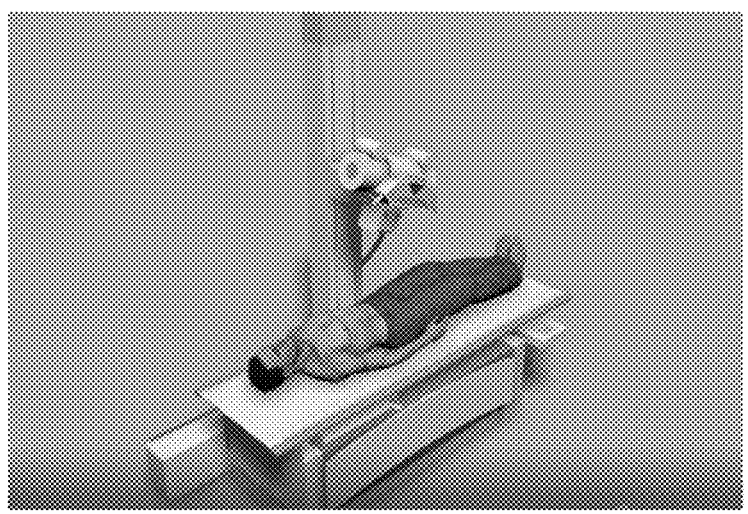
Figure 47:
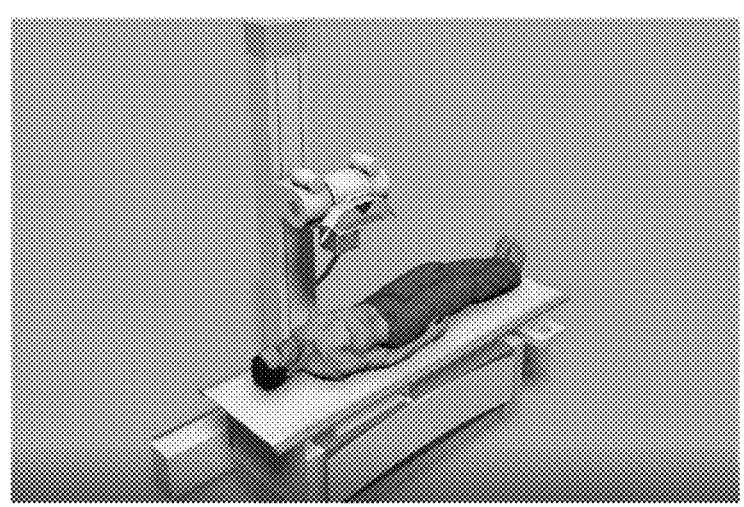

FIG. 14 shows a screening site 40 using a shielded area 42 and an embodiment of a spiral-trajectory tomosynthesis machine 10. FIG. 15 illustrates disinfecting of the shielded area 40 before a first patient is positioned within the shielded area 40. A spiral-trajectory tomosynthesis scan is performed on the first patient, as illustrated in FIGS. 17-20. The process is then repeated in FIGS. 21-27 for a second patient, and so on. Finally, FIG. 28 illustrates a final disinfecting step of the shielded area of FIG. 14, much like FIGS. 15 and 21, after all patients have been screened.

The following sources are indicated above as citations with a corresponding number and each is incorporated herein by reference:
1. The Utility of Digital Linear Tomosynthesis Imaging of Total Hip Joint Arthroplasty with Suspicion of Loosening: A Prospective Study in 40 Patients. Jan H. Göthlin and Mats Geijer. Biomed Res Int. 2013
2. Digital Breast Tomosynthesis: State of the Art. Srinivasan Vedantham, Andrew Karellas, Gopal R. Vijayaraghavan, Daniel B. Kopans. RSNA online publication, Nov. 24 2015, https://doi.org/10.1148/radiol.2015141303
3. Circular Tomosynthesis: Potential in Imaging of Breast and Upper Cervical Spine. Preliminary Phantom and in Vitro Study. Grant M Stevens 1, Robyn L Birdwell, Christopher F Beaulieu, Debra M Ikeda, Norbert J Pelc. Radiology, 2003 August; 228(2):569-75
4. Principles of Computerized Tomographic Imaging. Avinash C. Kak, Malcolm Slaney. IEEE Press, 1988.
5. Filtered back-projection for digital breast tomosynthesis with 2D filtering. Sean D. Rose, Emil Y. Sidky, Ingrid S. Reiser, Xiaochuan Pan. Proceedings Volume 10948, Medical Imaging 2019: Physics of Medical Imaging; 1094851 (2019)
6. Filtered Backprojection for Modifying the Impulse Response of Circular Tomosynthesis. G. M. Stevens 1, R. Fahrig, N. J. Pelc. Med Phys., 2001 March; 28(3): 372-80

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicants' contribution. The actual scope of the protection sought is intended to be defined in the following claims when viewed in their proper perspective based on the prior art.

What is claimed is:

1. A tomosynthesis scanning system comprising:
an X-ray emitter which emits photons during a scanning process and is connected to a first robotic device; and
an X-ray detector which detects the emitted photons during each of a plurality of accumulation cycles to create a digital signal for each of the plurality of accumulation cycles, and is connected to a second robotic device;
a processor which collects and stores the digital signal for each of the plurality of accumulation cycles of the X-ray detector as a plurality of stored projection views and reconstructs the plurality of stored projection views to produce 3-D images based on an algorithm operating on the processor, wherein the following 3-D images are produced as the algorithm operating on the processor:
reconstructs all of the plurality of stored projection views to produce a first of the 3-D images, $S_{full}$;
reconstructs all of the plurality of stored projection views acquired during a first half of the scanning process to produce a second of the 3-D images, $S_1$; and
reconstructs all of the plurality of stored projection views acquired during a second half of the scanning process to produce a third of the 3-D images, $S_2$;
wherein the first robotic device moves the X-ray emitter along a first conical-spiral trajectory path and the second robotic device moves the X-ray detector along a second conical-spiral trajectory path during the scanning process such that a symmetry axis of the emitted photons passes through a physical center of the X-ray detector.

2. The tomosynthesis scanning system of claim 1, wherein the movement of the X-ray emitter and the X-ray detector are synchronized.

3. The tomosynthesis scanning system of claim 1, further comprising a computer for controlling the first and second robotic devices.

4. The tomosynthesis scanning system of claim 1, wherein the first conical-spiral trajectory path is at least 360 degrees.

5. The tomosynthesis scanning system of claim 1, wherein the first robotic device moves the X-ray emitter to maintain a direct photon beam at the X-ray detector during scanning.

6. The tomosynthesis scanning system of claim 4, wherein the second conical-spiral trajectory path is at least 360 degrees.

7. The tomosynthesis scanning system of claim 4, wherein the first conical-spiral trajectory path is at least 720 degrees.

8. The tomosynthesis scanning system of claim 7, wherein the second conical-spiral trajectory path is at least 720 degrees.

9. A tomosynthesis scanning method comprising:
placing an object to be scanned between an X-ray emitter and an X-ray detector;
moving the X-ray emitter along a first conical-spiral path while emitting a photon beam at the X-ray detector which detects photons from the emitted photon beam during each of a plurality of accumulation cycles to create a digital signal for each of the plurality of accumulation cycles;
moving the X-ray detector along a second conical-spiral path;
allowing the photon beam to pass through the object before reaching the X-ray detector such that a symmetry axis of the emitted photon beam passes through a physical center of the X-ray detector;
collecting and storing the digital signal for each of the plurality of accumulation cycles of the X-ray detector as a plurality of stored projection views;
using the plurality of stored projection views to measure attenuation of the photon beam reaching the X-ray detector;
producing 3-D images based on the measured attenuation of the photon beam; and
reconstructing:
all of the plurality of stored projection views to produce a first of the 3-D images, $S_{full}$;
all of the plurality of stored projection views acquired during a first half of the scanning process to produce a second of the 3-D images, $S_1$; and
all of the plurality of stored projection views acquired during a second half of the scanning process to produce a third of the 3-D images, $S_2$.

10. The tomosynthesis scanning method of claim 9, wherein the second conical-spiral path is synchronized with the first conical-spiral path.

11. The tomosynthesis scanning method of claim 9, wherein the first conical-spiral path is at least 360 degrees.

12. The tomosynthesis scanning method of claim 11, wherein the first conical-spiral path is at least 720 degrees.

* * * * *